(12) United States Patent
Qiu

(10) Patent No.: US 8,563,503 B2
(45) Date of Patent: Oct. 22, 2013

(54) ANTIBIOTIC, ITS NUCLEOTIDE SEQUENCE, METHODS OF CONSTRUCTION AND USES THEREOF

(75) Inventor: Xiaoqing Qiu, Beijing (CN)

(73) Assignee: Protein Design Lab. Ltd., Beijing (CN)

( * ) Notice: Subject to any disclaimer, the term of this patent is extended or adjusted under 35 U.S.C. 154(b) by 144 days.

(21) Appl. No.: 13/022,512

(22) Filed: Feb. 7, 2011

(65) Prior Publication Data
US 2012/0202734 A1  Aug. 9, 2012

(51) Int. Cl.
| | |
|---|---|
| *A01N 37/18* | (2006.01) |
| *A61K 38/00* | (2006.01) |
| *A61P 31/04* | (2006.01) |
| *C12P 21/06* | (2006.01) |
| *C12N 15/00* | (2006.01) |
| *C07K 1/00* | (2006.01) |
| *C07K 14/00* | (2006.01) |
| *C07K 17/00* | (2006.01) |
| *C07H 21/04* | (2006.01) |

(52) U.S. Cl.
USPC ........ 514/2.4; 530/350; 536/23.7; 435/320.1; 435/69.1

(58) Field of Classification Search
None
See application file for complete search history.

(56) References Cited

FOREIGN PATENT DOCUMENTS

| CN | ZL200510020219.9 | 8/2005 |
| CN | 101643501 A * | 2/2010 |

OTHER PUBLICATIONS

Qiu et al, Major transmemebrane movement soociated with colicin Ia channel gating. J. Gen. Physiology, 107:313-328 (1996).
Ji et al, Cell density control of staphyliccocal virulence mediated by an octapeptide pheromone. Proc. Natl. Acad. Sci. USA, 92:12055-12059 (1995).

\* cited by examiner

*Primary Examiner* — Cecilia J Tsang
*Assistant Examiner* — Zachary J Miknis
(74) *Attorney, Agent, or Firm* — Maschoff Brennan

(57) ABSTRACT

The present invention belongs to field of biology and medicine, and especially relates to a novel antibiotic, its nucleotide sequence, methods of construction and uses thereof. A novel antibiotic, wherein the end of any peptide of the allosteric colicin is connected linearly to the end of peptide of the *Staphylococcus aureus* pheromone AgrD I, AgrD II, AgrD III, AgrD IV or *Staphylococcus epidermidis* pheromone. Wherein the allosteric colicin being yielded by artificially mutating the amino acid residues G11A, H22R, A26G, V31L and H40K in the peptide chain of wild type Colicin E1, Ia, Ib, A, B, N, or their ion channel-forming structural domain. In comparison with the traditional antibiotics, the novel antibiotics in the present invention are not likely to lead to drug resistance and cause hypersensitivity reaction.

16 Claims, 7 Drawing Sheets

ANTIBIOTIC, ITS NUCLEOTIDE SEQUENCE, METHODS OF CONSTRUCTION AND USES THEREOF

FIELD OF THE INVENTION

The present invention belongs to the domain of biology and medicine, and in detail especially relates to a novel antibiotic, its nucleotide sequence, methods of construction and uses thereof.

RELATED ART

Since Penicillin and other antibiotics were brought into use in 1944, bacteriums, in particular pathogens, which threaten life, such as *Staphylococcus aureus, Streptococcus pneumoniae, Pseudomonas aeruginosa, Mycobacterium tuberculosis* and others have acquired drug resistance. According to reports published by United States Disease Control Center (CDC) in previous years, these antibiotics may be completely useless in 10 or 20 years.

The present antibiotics kill pathogenic bacteria by restraining synthesis of cell wall, and restraining or disturbing the pathway of bacterial nucleic acid and protein metabolism and synthesis. However, these antibiosis modes are more likely to lead to drug resistance by bacteria mutation. Therefore, scientists are dedicated to develop novel antibiotics. In nature, a number of bacterial toxins can directly form ion channels on bacteria cytomembrane to kill bacteria. The typical specimen is a kind of bacterial toxin-colicin secreted by *E. coli*. One of which is Colicin Ia, found in 1952. The transmembrane spatial structure of colicin Ia when ion channel is open as well as shut on the artificial lipide bimolecular film (Qiu et al, Major transmemebrane movement associated with colicin Ia channel gating. J. Gen. Physiology, 107:313-328 (1996)) was disclosed in 1996. This established theoretical basis for designing and preparing novel antibiotics on molecular level.

Recently, it has been found that bacteria secrete signal transduction polypeptides out of the cells. These polypeptides are able to find and combine the corresponding receptors on homogeneous bacteria's cytomembrane, and then transduce the signal into bacteria. These transduction polypeptides are usually composed of several or dozens of amino acids, such as pheromone AgrD of *Staphylococcus aureus*, which is one peptide containing 8 amino acids (Ji et al, Cell density control of staphyliccocal virulence mediated by an octapeptide pheromone. Proc. Natl. Acad. Sci. USA, 92:12055-12059 (1995)).

As mentioned above, colicin is an ideal ion channel antibiotic model, but wild-type colicin can only act on *E. coli* which is a homogeneous heterologous strain, so there is a need of changing colicin's targeting so as to make it turn to attack other kinds of pathogen. Moreover, there are amino acid residues which are likely to cause hypersensitive reaction in the peptide chain of wild-type colicin, wherein hypersensitive reaction means abnormal and extravagant immune response. If a pheromone which is specific for pathogen can be used as inducer to change the targeting of colicin, it should be an ideal direction of antibiotic exploitation. The inventor of the present invention has obtained the patent right (Patent No. ZL200510020219.9) in which the pheromone gene of *E. coli* was linked to the pheromone gene of *Streptococcus albus* to encode antifungal polypeptide. However, there are some structure domains which may cause hypersensitive reaction in colicin peptides, so there is a need to make improvement.

SUMMARY OF THE INVENTION

To overcome the above technical defects and make up a deficiency in the art, the present invention provides a novel antibiotic and nucleotide sequence encoding it, preparation method and uses thereof. The antibiotic contains colicin, and can be capable of killing pathogens without injuring human normal cells. So the present invention overcomes the defect of hypersensitivity caused by colicin.

An allosteric colicin being yielded by artificially mutating the amino acid residues G11A, H22R, A26G, V31L and H40K in the peptide chain of wild type Colicin E1, Ia, Ib, A, B, N, or their ion channel-forming structural domain is provided by the present invention.

One of the allosteric colicins is yielded by mutating wild-type Colicin Ia, and comprises the amino acid sequence as set forth in SEQ ID NO: 36.

The present invention provides nucleotide molecules encoding the peptides of the allosteric colicins.

The present invention provides use of said allosteric colicins for manufacturing antibacterial medicament.

The present invention provides a novel antibiotic, wherein the end of any peptide of the allosteric colicin is connected linearly to the end of peptide of the *Staphylococcus aureus* pheromone AgrD I, AgrD II, AgrD III, AgrD IV or *Staphylococcus epidermidis* pheromone.

One of the allosteric colicin is yielded by artificially mutating wild-type Colicin Ia, and linking the N-terminus of any peptide of said *Staphylococcus aureus* pheromone AgrD I, AgrD II, AgrD III, AgrD IV or *Staphylococcus epidermidis* pheromone to C-terminus of peptide of said allosteric colicins of Ia to form the connected peptides with amino acid sequences as set forth in SEQ ID Nos. 13, 15, 17, 19 or 21 respectively.

The C-terminus of a *Staphylococcus aureus* pheromone AgrD I is connected to the N-terminus of the peptide of said allosteric peptide of Ia to form a fusion peptide with amino acid sequence as set forth in SEQ ID NO. 23.

The prevent invention provides nucleotide molecules encoding any of said novel antibiotics.

The present invention provides nucleotide molecules with nucleotide sequences set forth in SEQ ID Nos: 12, 14, 16, 18, 20 or 22.

The present invention provides a recombinant plasmid comprising any of the nucleotide molecules.

The present invention provides uses of any of the novel antibiotics for manufacturing antibacterial medicament.

The present invention provides methods of construction of any of the novel antibiotics, wherein any of the recombinant plasmids is transfected into the expression system to express the polypeptide, and the polypeptide is separated and purified to obtain the novel antibiotic.

The expression system is colon *bacillus* engineering bacteria *E. coli* BL-21.

In the present invention, to prevent hypersensitivity of a host caused by peptide fragments on N-terminus of wild type colicin, the amino acid residues G11A, H22R, A26G, V31L and H40K in these peptide fragments were mutated selectively in advance. The mutation may depress potential immunogenicity. As a result nucleotide sequence encoding allosteric colicin and amino acid sequence of said allosteric colicin were obtained. The allosteric colicin preserved ion channel-forming activity of wild type colicin. It is able to kill a strain of *E. coli*. The wild type colicins could be selected from colicin E1, Ia, Ib, A, B, N or ion channel-forming structural domain thereof.

In preferred embodiments of the present invention wild type Colicin Ia was selected to mutate to be Ia'. As shown in FIG. 7, the peptide of Ia' was operably linked to peptide chains of pathogen pheromones. The obtained peptides, i.e. the novel antibiotics of this invention, in which the pathogen pheromones contained are capable of changing the targeting of Ia' contained, and make the novel antibiotics attack other pathogen strains. Its mechanism is as follows: the pheromone contained can bond to receptors in the cytomembrane of a target pathogen and induce allosteric peptide to arrive at a target pathogen cytomembrane, and then the allosteric peptides form fatal ion channel on the target pathogen cytomembrane. The contents of the target pathogen pathogen are leaked out, and make the target pathogen die.

In preferred embodiments of present invention, the peptide chain of Ia' is connected to the peptide chain of *Staphylococcus aureus* pheromone AgrD I, AgrD II, AgrD, AgrD IV or *Staphylococcus epidermidis* pheromone linearly. As shown in FIG. 1-5, the peptide chain of *Staphylococcus aureus* pheromone AgrD I, AgrD II, AgrD, AgrD IV or *Staphylococcus epidermidis* pheromone was introduced following C-terminus of the allosteric peptide of Ia to form 5 kinds of connected peptide with amino acid sequence as SEQ ID NOs. 13, 15, 17, 19 or 21 respectively. From Embodiments 4, 5, 6, and 7 and table 1, 2, it is observed the 5 kinds of connected peptide have bactericidal effect. While, when five kinds of *Stapylococcus* pheromone are respectively inserted into the first position i.e. N-terminus of the allosteric peptide of Ia to form other 5 kinds of connected peptide chains. As shown in FIG. 6, from the experiment result, we found that only the connected peptide chain of AgrD I and Ia', its amino acid sequence as SEQ ID NO. 23, has antibacterial effect on *Pseudomonas aeruginosa*.

The nucleotide sequences of nucleic acid molecules encoding the allosteric colicin peptide and the novel antibiotics obtained in the present invention could be adjusted due to the degeneracy of codons. That means any nucleic acid molecules encoding novel antibiotics in the present invention belongs to the scope of rights of the present invention.

The nucleic acid molecules encoding novel antibiotics in the present invention were cloned into plasmid to obtain recombinant plasmids which are able to express the novel antibiotics of the present invention in host cell. In the present invention, the original plasmid pSELECT™-1 plasmid was purchased from Promega Corporation, which was firstly cloned in genes of allosteric colicin peptide and immunity protein. The nucleotide sequence encoding *Stapylococcus* pheromone was inserted into the N-terminus or N-terminus of gene of allosteric polypeptide by Double Strands Oligonucleotide Point Mutation Technology (QUICKCHANGE™ Kit, Strategene Corporation) according to the manipulation of Strategene corporation medical kit to form the recombinant plasmid of the present invention. As shown in FIG. 1-6, the nucleotide sequences encoding 5 kinds of *Stapylococcus* pheromones were introduced following 626 amino acid residue position of colicin Ia' (i.e. carboxyl end) or inserted into the first amino acid residue position (i.e. initiator codon) to form six kinds of recombination plasmids which express fusion peptides with antimicrobial activity in the present invention.

The preparation method of the novel antibiotic in the present invention is that the above recombinant plasmids were transfected into *E. coli* engineering bacterium to obtain transgeneic *E. coli* which can generate novel antibiotic, the fusion protein expressed by the transgeneic *E. coli* was separated and purified to obtain the novel antibiotics of the present invention. *E. coli* engineering bacterium strain BL-21 is preferred in the present invention.

The novel antibiotics obtained in the present invention can be used for manufacturing medicament which treat or prevent the infectious of *E. coli, Staphylococcus aureus, Staphylococcus epidermidis, Pseudomonas aeruginosa*. The novel antibiotics obtained in the present invention can be appended into a pharmaceutically acceptable carrier or excipient or other ingredients to prepare the medicine compounds applied on clinic.

In comparison with the traditional antibiotics, the novel antibiotics in the present invention are not likely to lead to drug resistance and cause a hypersensitivity reaction. As the experimental result of embodiment 10 shows, compared with recombination antibiotics constructed by wild type colicin, the valence of mouse sera immunized by allosteric colicin peptide or novel antibiotic of the present invention is lower by two orders of magnitude. The bacteria are likely to acquire drug resistance to traditional antibiotics through altering their cell wall structures, as well as the metabolism of nucleic acid and protein by generating β-lactamase, reducing intaking and changing drug action site and others by mutation. The bacteria can not easily repair the defect of cytomembrane integrality caused by the novel antibiotics of this invention by mutation because such defects can result in bacteria dying in a few minutes. The novel antibiotics in the present invention possess bactericidal effects on drug resistance bacterium that other antibiotics can't be comparable with. The experimental data shows that the novel antibiotics possess wonderful bactericidal effect, and two kinds of antibiotics (PMC-SA1, PMC-SA) are indicative of excellent in vivo protective action to experimental mice.

EMBODIMENTS

The invention is further illustrated by the following embodiments as well as the drawings.

Embodiment 1

Figure 1:
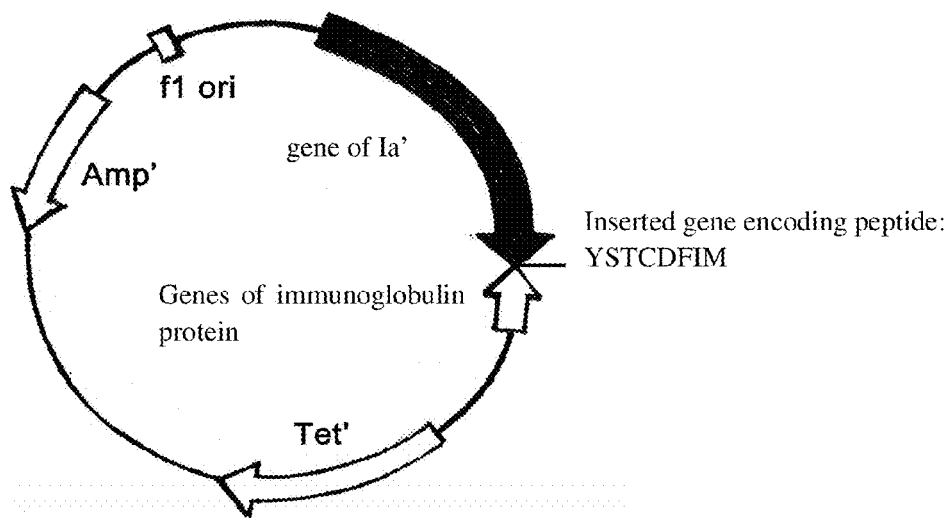
FIG. 1 schematically depicts the structure of a recombinant plasmid that contains gene of *Staphylococcus aureus* pheromone AgrD I and gene of Ia' to form a plasmid referred to herein as pBHC-SA1 encoding for peptide YSTCDFIM (SEQ ID NO: 2).
Figure 2:
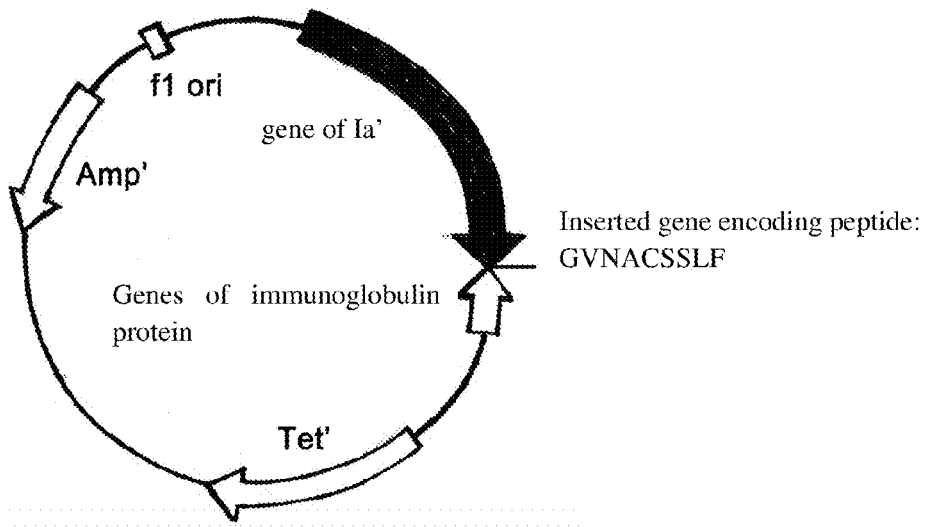
FIG. 2 schematically depicts the structure of a recombinant plasmid that contains gene of *Staphylococcus aureus* pheromone AgrD II and gene of Ia' to form a plasmid referred to herein as pBHC-SA2 encoding peptide GVNACSSLF (SEQ ID NO: 4).
Figure 3:
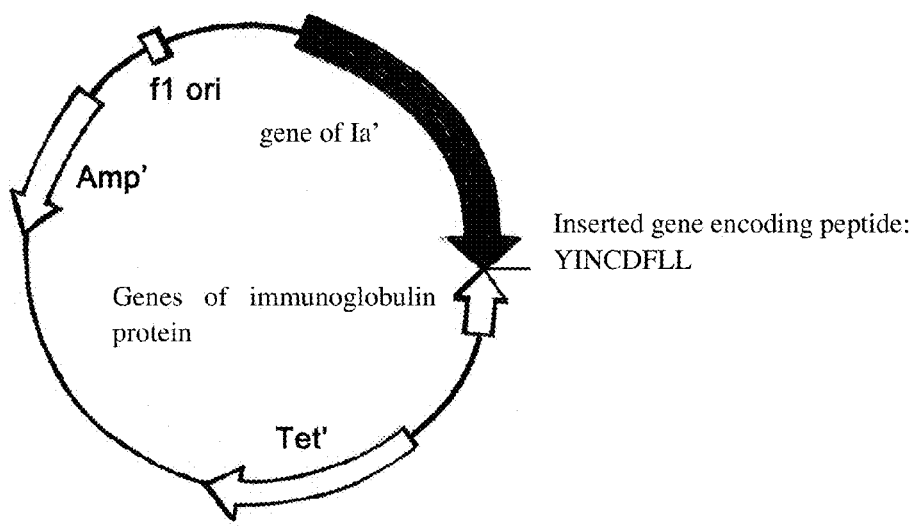
FIG. 3 schematically depicts the structure of a recombinant plasmid that contains gene of *Staphylococcus aureus* pheromone AgrD III and gene of Ia' to form a plasmid referred to herein as pBHC-SA3 encoding peptide YINCDFLL (SEQ ID NO: 6).
Figure 4:
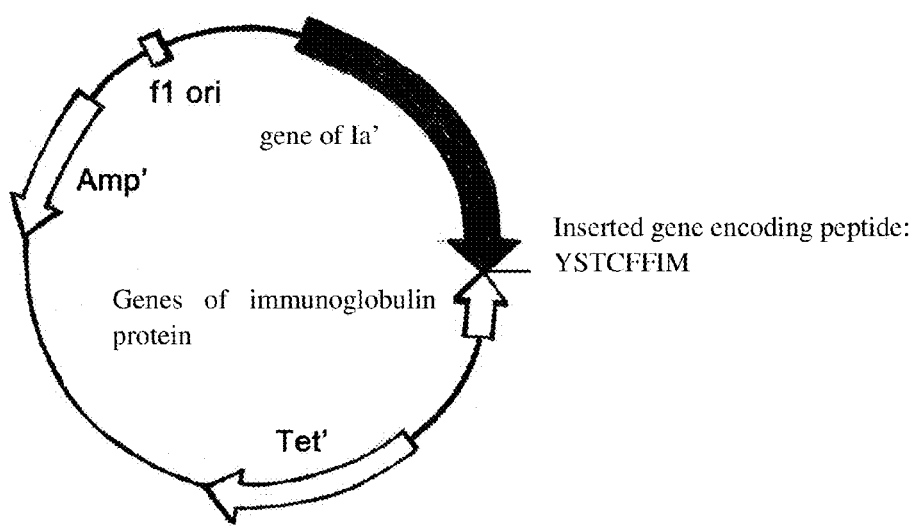
FIG. 4 schematically depicts the structure of a recombinant plasmid that contains gene of *Staphylococcus aureus* pheromone AgrD IV and gene of allosteric colicin peptide Ia' to form a plasmid referred to herein as pBHC-SA4 encoding peptide YSTCFFIM (SEQ ID NO: 8).
Figure 5:
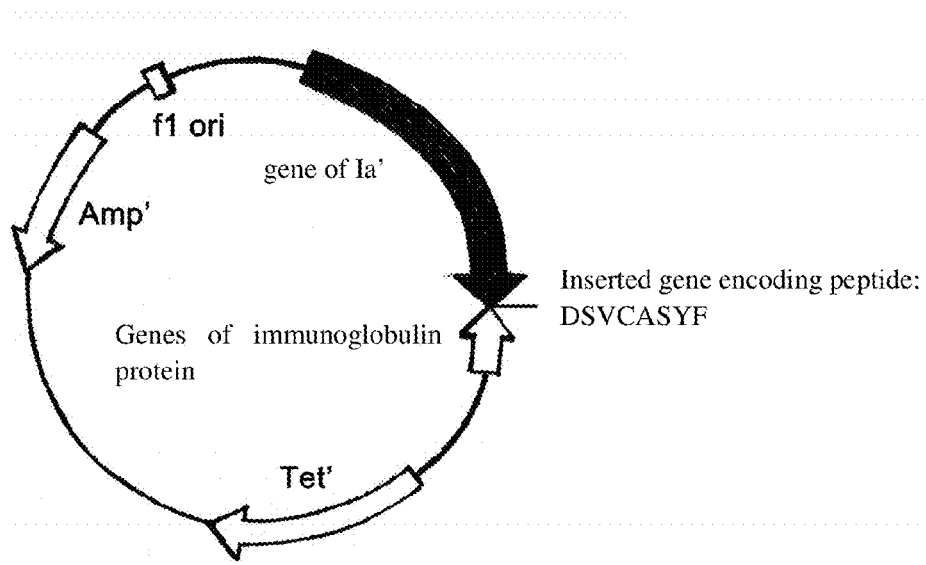
FIG. 5 schematically depicts the structure of a recombinant plasmid that contains gene of *Staphylococcus epidermidis* pheromone and gene of Ia' to form a plasmid referred to herein as pBHC-SE encoding peptide DSVCASYF (SEQ ID NO: 10).
Figure 6:
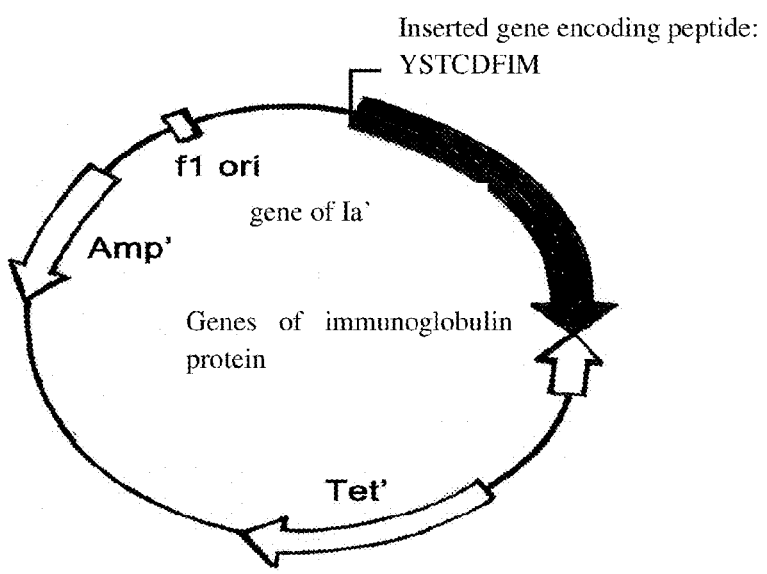
FIG. 6 schematically depicts the structure of a recombinant plasmid that contains gene of *Staphylococcus aureus* pheromone AgrD I and gene of allosteric colicin peptide Ia' to form a plasmid referred to herein as pBHC-PA encoding peptide YSTCDFIM (SEQ ID NO: 2), wherein AgrD I gene was inserted into the first amino acid residue of allosteric peptide Ia's gene.
Figure 7:
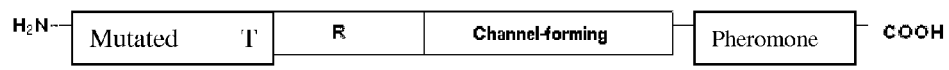
FIG. 7 illustrates the construction of the novel antibiotic peptide. Wherein T, R are two signal identification structure domains situated at the N-terminus of allosteric colicin peptide therein a part of amino acid residues in T structure domain have already been mutated. Channel-forming is a structure domain capable of forming ion channel, which is situated at the C-terminus of allosteric colicin peptide. The pheromone was fused following the C-terminus of Ia' peptide.

Construction of Plasmid Expressing the Novel Antibiotics and Preparation of the Novel Antibiotic The original plasmid was pSELECT™-1 plasmid (8.3 kb) (purchased from Promega Corporation), which was cloned genes of allosteric colicin peptide Ia' (set forth in SEQ ID NO:11) and immunity protein at its multiple clone site. By Double Strands Oligonucleotide Point Mutation Technology (QUICKCHANGE™ Kit, Strategene corporation), the genes of pheromone of *Staphylococcus* set forth in SEQ ID NOs. 1, 3, 5, 7 and 9 were introduced following the codon of I626 amino-acid residue of Ia' respectively to form a series of recombinant plasmids, herein referred as pBHC-SA1, pBHC-SA2, pBHC-SA3, pBHC-SA4 and pBHC-SE shown in FIG. 1-5, which are capable of expressing novel antibiotics. While, the peptide of pheromone AgrD I with amino acid sequence set forth in SEQ ID No. 1 was introduced in front of the codon of 1st amino-acid residue of Ia' to form the recombinant plasmid pBHC-PA as shown in FIG. 6. These recombinant plasmids were respectively transfected into *E. coli* BL-21 engineering bacterium to prepare novel antibiotics.

The mutation procedure was operated according to the manual of Strategene QUICKCHANGE™ Site Directed Mutagenesis Kit (catalog #200518):

1. points mutation reactant was prepared:
5 µl 10× buffer
2 µl (10 ng) original plasmid pSELECT™-1 with genes of Ia' and immunity protein
1.25 µl (125 ng) artificial 5'-3' oligonucleotide primer (refer to the even number sequence of SEQ ID NOs.24-34)
1.25 µl (125 ng) artificial 3'-5' oligonucleotide primer (refer to the odd number sequence of SEQ ID Nos.24-34)
1 µl dNTP
50 µl de-ionized water
1 µl pfu
(The above drugs were all reagents in the medical kit, except plasmid, primer and de-ionized water.)

2. PCR amplification was proceeded according to amplification condition as follow: denature at 95° C. for 35 seconds, anneal at 53° C. for 70 seconds, extend at 68° C. for 17 minutes, totally 20 cycles;

3. 1 µl Dpn 1 endoenzyme was incorporated to digest parent DNA chain (37° C., 1 h), 1 µl reactant was taken to ice and incubated with 50 µl XL1-Blue competent cells for 30 minutes, heat shock at 42° C. for 45 seconds, and then taken into ice for 2 minutes;

4. 0.5 ml NZY culture medium was added, the bacteria solution (reactant of step 3, i.e. transformed cells from competent cells) was shaken at 220 rpm, 37° C. for 1 hour, 50-100 µl reactant was take out to plank (LB culture medium added in 1% agar, 50 µg/ml ampicillin, at 37° C. over night);

5. The bacteria was picked out after cultivating 18 hours, the plasmid was abstracted and sequenced to ascertain its mutation had been successful;

6. 100 ng mutation plasmid was placed on ice and incubated with 40 µl of BL-21 competent cells for 5 minutes, heat shock at 42° C. for 30 seconds, and then taken into ice for 2 minutes. 160 µl SOC culture medium was added, bacterium was shaken at 220 rpm, 37° C. for 1 hour and take out to plank (LB culture medium added 1% agar, 50 µg/ml ampicillin, at 37° C. over night), mono-clone colony was picked out for largely reproducing the bacterium;

7. the bacterium was largely reproduced, with 8-10L FB culture medium, at 250 rpm, 37° C. for 3-4 hours. IPTG was added, at 250 rpm, 28° C. for regrowing 4 hours. The thallus was centrifugated at 4° C., 6000 g for 20 minutes, and then was suspended in 80-100 ml of 50 mM boric acid buffer fluid (pH 9.0, 2 mM EDTA) at 4° C. 50 µg PMSF was added, and then the thallus was ultrasonicated (at 4° C., 400 W for 1 minute, repeat for 4-5 times with interval 2-3 minutes, ensuring the temperature of the bacteria solution). The cracked thallus was high-speed centrifuged (at 4° C., 75,000 g for 90 minutes). The 5,000,000 unit streptomycin sulfate was added into the supernatant to deposit DNA (stirring at 4° C. for 1 hour). After centrifuged at 10000 g, 4° C. for 10 minutes, the supernatant was loaded in bag filter of molecular weight 15,000 at 4° C. After dialysed by 10 L of 50 mM boric acid buffer fluid over night, the supernatant was centrifuged at 10000 g, 4° C. for 10 minutes again. The supernatant was loaded on CM ion-exchange column, washed thoroughly, eluted by 0.3 M NaCl+50 mM boric acid buffer fluid to obtain the novel antibiotic. Corresponding to the above 6 kinds of recombination plasmid, 6 kinds of novel antibiotics named PMC-SA1, PMC-SA2, PMC-SA3, PMC-SA4, PMC-SE and PMC-PA can be obtained respectively.

The artificial oligonucleotide sequences for preparing pheromone gene of the above 6 kinds of mutation plasmid are respectively as follows:

Embodiment 2

Inhibiting Effect of the Novel Antibiotics on Penicillin Sensitive *Staphylococcus aureus*

The bacterium was United States Reference Culture ATCC 25923 penicillin-sensitive *Staphylococcus aureus*. 2 microliter of bacteria solution ($10^5$ CFU/ml) was added into 10 ml culture solution containing 1% tryptone, 1% NaCl, 0.5% yeast extract, 0.5% glucose and 0.1% $K_2HPO_4$, totally prepared six groups. The first group as control was added 0.3 M NaCl+50 mM boric acid buffer fluid (i.e. blank preservative fluid for novel antibiotic, wild-type colicin Ia and protein produced by BL-21 engineering bacteria without plasmid, by the same volumes of antibiosis polypeptide liquid in the experimental group, the second group was added penicillin G sodium by 100 ng/ml, the third group was added wild-type colicin Ia by 100 ng/ml, the fourth group was added protein

```
pBHC-SA1
5'-3'
                                                                        (SEQ ID NO. 24)
gcg aat aag ttc tgg ggt att TAT TCC ACC TGT GAT TTT ATA ATG taa ata aaa tat aag aca ggc 3'-5'
                                                                        (SEQ ID NO. 25)
gcc tgt ctt ata ttt tat tta CAT TAT AAA ATC ACA GGT GGA ATA aat acc cca gaa ctt att cgc pBHC-SA2
5'-3'
                                                                        (SEQ ID NO. 26)
gcg aat aag ttc tgg ggt att GGA GTT AAC GCA TGT TCT TCC CTG TTT taa ata aaa tat aag aca ggc 3'-5'
                                                                        (SEQ ID NO. 27)
gcc tgt ctt ata ttt tat tta AAA CAG GGA AGA ACA TGC GTT AAC TCC aat acc cca gaa ctt att cgc pBHC-SA3
5'-3'
                                                                        (SEQ ID NO. 28)
gcg aat aag ttc tgg ggt att TAT ATA AAC TGT GAT TTT CTT CTG taa ata aaa tat aag aca ggc 3'-5'
                                                                        (SEQ ID NO. 29)
gcc tgt ctt ata ttt tat tta CAG AAG AAA ATC ACA GTT TAT ATA aat acc cca gaa ctt att cgc pBHC-SA4
5'-3'
                                                                        (SEQ ID NO. 30)
gcg aat aag ttc tgg ggt att TAT TCC ACC TGT TAC TTT ATA ATG taa ata aaa tat aag aca ggc 3'-5'
                                                                        (SEQ ID NO. 31)
gcc tgt ctt ata ttt tat tta CAT TAT AAA GTA ACA GGT GGA ATA aat acc cca gaa ctt att cgc pBHC-PA
5'-3'
                                                                        (SEQ ID NO. 32)
gga tga agg aga tac cga atg TAT TCC ACC TGT GAT TTT ATA ATG tct gac cct gta cgt att aca 3'-5'
                                                                        (SEQ ID NO. 33)
gtg aat acg tac agg gtc aga CAT TAT AAA ATC ACA GGT GGA ATA cat tcg gta tct cct tca tcc pBHC-SE
5'-3'
                                                                        (SEQ ID NO. 34)
gcg aat aag ttc tgg ggt att GAT TCC GTT TGT GCA TCC TAT TTT taa ata aaa tat aag aca ggc 3'-5'
                                                                         (SEQ ID NO.35)
gcc tgt ctt ata ttt tat tta AAA ATA GGA TGC ACA AAC GGA ATC aat acc cca gaa ctt att cgc
``` produced by BL-21 engineering bacteria without plasmid by 100 ng/ml, the fifth group was added recombinant protein that C-terminus of colicin Ia is fused other eight peptides by 100 ng/ml, and the sixth group was added the novel antibiotic PMC-SA1 by 100 ng/ml.

Figure 8:
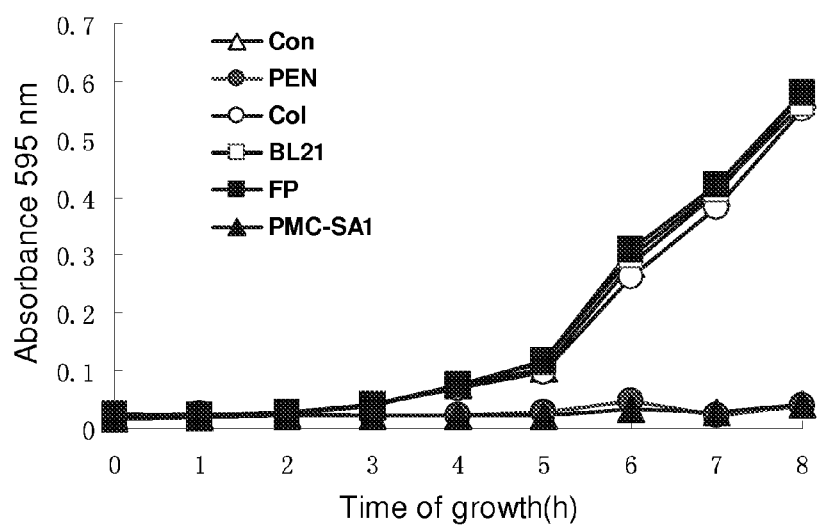
FIG. 8 shows the result of experiment for the bactericidal activity of the novel antibiotic PMC-SA1 on the methicillin-sensitive *Staphylococcus aureus*. Wherein Con means control; PEN means penicillin; COL means wild-type colicin; BL21 means proteins produced by BL-21 engineering bacterium without plasmid; FP means recombinant proteins yielded by fusing other eight peptides following the C-terminus of colicin Ia PMC means PMC-SA1. The drug dosage is 100 ng/ml in each experimental group.

The solutions of the six groups were respectively put into 100 ml conical flask, 200 rpm, grew at 37° C. 100 μl was sampled per hour, and added onto 96 hole ELISA Plate and measured bacterium growth cloudiness by spectrophotometer (A595 nm) color comparison. The bacteria-growth curve was drawn up to compare the bacteriostasis efficacy of novel antibiosis. The result is shown in FIG. 8, which shows that penicillin-sensitive *Staphylococcus aureus* can only be restrained by penicillin as well as PMC-SA1.

Embodiment 3

Transmission Electron Microscope Observations of the Bactericidal Effect of the Novel Antibiotic PMC-SA1 on Methicillin-Resistant *Staphylococcus aureus* (ATCC BAA-42) (Dyed by 1% Phospho-Wolframic Acid, Magnified by 25,000 Fold)

Culture solution: 1% tryptone, 1% NaCl, 0.5% yeast extract, 0.5% glucose, 0.1% $K_2HPO_4$.
Con: control group, the bacterium was added to the above culture solution and proper amount of 0.3 M NaCl+50 mM boric acid buffer solution, 200 rpm, grew at 37° C. for 2 hours, and the bacterial appearance was still regular;
Oxa: the bacterium was added to the above culture solution with 500 μg/ml Oxacillin, 200 rpm, grew at 37° C. for 1.5 hours, the colour as well as appearance of the bacterium had changed, but the thallus was still integrated;
PMC: the bacterium was added to the above culture solution with 10 μg/ml PMC-SA1 for 0.5 hours. And then the bacterium ruptured and leaked out its contents.

Figure 9:
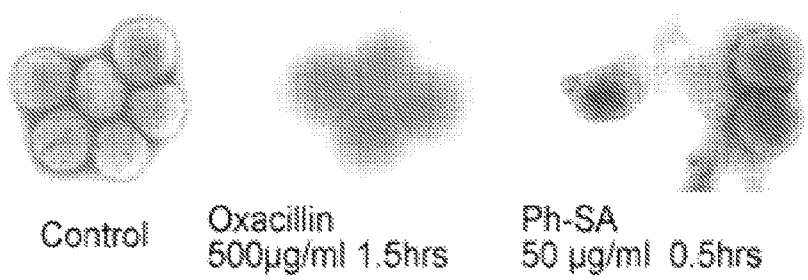
FIG. 9 shows the transmission electron microscope observation of the bactericidal effect of PMC-SA1 on methicillin-resistant *Staphylococcus aureus* (ATCC BAA-42) (magnified by 25,000 times). Con means control. The appearance of bacterium was regular. Oxa, disposed with oxacillin (500 µg/ml) for one hour and a half, the appearance of bacterium had changed, but thallus were still integrative. PMC: disposed with PMC-SA1 (10 µg/ml) for half an hour, bacterium were ruptured, the contents were leaked out.

As shown in FIG. 9, the sterilize mechanism of the novel antibiotic was completely different from that of penicillin. 500 μg/ml oxacillincan could damage methicillin-resistant *Staphylococcus aureus*, while 10 μg/ml PMC-SA1 could kill methicillin-resistant *Staphylococcus aureus* effectively. The molecular weight of PMC-SA1 molecule (about 70,000 daltons) is 160 times to that of oxacillin molecule (about 450 daltons), while the concentration of PMC-SA1 used in this embodiment was 1/50 times to that of oxacillin, therefore the antibiosis effect shown by PMC-SA1 in this embodiment was about eight thousand folds more powerful than oxacillin.

Embodiment 4

In Vitro Antibacterial Activity of Novel Antibiotic PMC-SA1

1. Experimental Materials
(1) Drugs
PMC-SA1: 1.5 mg/ml.
Cefazolin Sodium for Injection: 0.5 g/bottle, produced by North China pharmaceutical Group Corporation.
Benzylpenicillin Sodium for Injection: 800,000 U/bottle, produced by North China pharmaceutical Group Corporation.
Ampicillin Sodium for Injection: 1 g/bottle, produced by North China pharmaceutical Group Corporation.
Oxacillin Sodium for Injection: 0.5 g/bottle, produced by North China pharmaceutical Group Corporation.
Vancomycin, 2.5 mg/ml.

The above drugs were dissolved and diluted by sterilized water. The final concentrations of each drug were 128 mg/L, 64 mg/L, 32 mg/L, 16 mg/L, 8 mg/L, 4 mg/L, 2 mg/L, 1 mg/L, 0.5 mg/L, 0.25 mg/L, 0.125 mg/L, 0.06 mg/L, 0.03 mg/L and 0.015 mg/L.

(2) Bacteria
Clinical isolated strain: All of the bacteria are identified by laboratory bacteria room of West China University of Medical Sciences that collected and separated the culture.
*Staphylococcus aureus* (28 strains, wherein MRSA 10 strains, MSSA 18 strains), *Staphylococcus epidermidis* (10 strains, wherein MRSA 5 strains, MSSE 5 strain), *Enterococcus faecalis* (5 strains), *E. coli* (10 strains), *Baumanii* (10 strains), totally 63 strains.
Standard quality control strain: penicillin-sensitive *Staphylococcus aureus* ATCC 25923, penicillin-resistant *Staphylococcus aureus* ATCC 29213, methicillin-resistant *Staphylococcus aureus* ATCC BAA-42, vancomycin-resistant *Enterococcus faecalis* ATCC 700802.

(3) Culture Solution
MH Broth Culture Solution: 25 g was added into 100 ml distilled water, heat to dissolve, subpackaged, autoclaved at 116° C. for 20 minutes, and MH Solid Culture Medium, 36 g was added into 1000 ml distilled water, autoclaved at 116° C. for 20 minutes, used for drug sensitive test of Gram-positive and negative aerobic bacteria.
Blood culture solution for *Enterococcus faecalis*, which was prepared by adding defibration rabbit blood into the MH culture solution by 5-10% and cultured at 37° C. in 5% $CO_2$ for 24 hours.

2. Experimental Methods
(1) The Measurement of Minimum Inhibitory Concentration (MIC)
The Minimum Inhibitory Concentration (MIC) of PMC-SA1 was measured by Agar Doubling Dilution Method. The bacterium was inoculated on the surface of agar plate containing different concentration of drugs by multipoint inoculate instrument (Deneley A400). The bacterial content per point was $10^5$ CFU/ml. After incubated at 37° C. for 18-24 hours, the result can be observed. The least concentration of drugs in plate culture solution without bacterium growing was Minimum Inhibitory Concentration (MIC) of the drug to the said bacteria.

3. Results
Laboratory results were shown in Table 1.

TABLE 1

Comparison of in vitro bactericidal activity of PMC-SA

| Strain (amount) | Drugs | $MIC_{50}$ (mg/L) | $MIC_{90}$ (mg/L) | Scope of MIC(mg/L) |
|---|---|---|---|---|
| *Staphylococcus aureus* (MRSA) | PMC-SA1 | 8-16 | >16 | <0.25-64 |
| | Cefazolin | >128 | >128 | 1-128 |
| | Penicillin | 128 | >128 | 1-128 |
| | Ampicillin | 16 | 32 | 0.06-64 |
| | Oxacillin | >128 | >128 | 0.5-128 |
| | Vancomycin | 0.25 | 1 | 0.004-2 |
| *Staphylococcus aureus* (MSSA) | PMC-SA1 | 0.5 | 16 | 0.06->32 |
| | Cefazolin | 0.125 | 0.25 | <0.015-0.5 |
| | Penicillin | 8 | 64 | 0.125->128 |
| | Ampicillin | 0.25 | 1 | <0.015-0.025 |
| | Oxacillin | 0.125 | 0.125 | <0.015-0.25 |
| | Vancomycin | 0.5 | 1 | 0.03-1 |
| *Staphylococcus epidermidis* | PMC-SA1 | >64 | >64 | 1->128 |
| | Cefazolin | 32 | >128 | 0.06->128 |

TABLE 1-continued

Comparison of in vitro bactericidal activity of PMC-SA

| Strain (amount) | Drugs | MIC$_{50}$ (mg/L) | MIC$_{90}$ (mg/L) | Scope of MIC(mg/L) |
|---|---|---|---|---|
| (MRSE) | Penicillin | >128 | >128 | 8->128 |
| | Ampicillin | 16 | 64 | 0.06-64 |
| | Oxacillin | 64 | >128 | 0.5->128 |
| | Vancomycin | 0.5 | 1 | 0.25-2 |
| Staphylococcus epidermidis (MSSE strain) | PMC-SA1 | 1 | 32 | 0.25-64 |
| | Cefazolin | 0.03 | 0.5 | <0.125-0.5 |
| | Penicillin | 4 | 32 | 0.125-128 |
| | Ampicillin | 0.03 | 0.25 | <0.125-0.25 |
| | Oxacillin | 0.03 | 0.125 | <0.125-0.25 |
| | Vancomycin | 0.5 | 0.5 | 0.06-0.5 |
| Enterococcus | PMC-SA1 | >64 | >64 | 8->128 |
| | Cefazolin | 32 | >128 | 32->128 |
| | Penicillin | 32 | 64 | 32->128 |
| | Ampicillin | 0.5 | 16 | 0.25-16 |
| | Oxacillin | 16 | >128 | 8->128 |
| | Vancomycin | 1 | 2 | 0.5-50 |
| E. coli | PMC-SA1 | 16 | >32 | 4->16 |
| | Cefazolin | >128 | >128 | 128->128 |
| | Penicillin | >128 | >128 | >128 |
| | Ampicillin | >128 | >128 | 16->128 |
| | Oxacillin | >128 | >128 | >128 |
| | Vancomycin | >128 | >128 | >128 |
| Baumanii | PMC-SA1 | 32 | >64 | 0.5->64 |
| | Cefazolin | >128 | >128 | >128 |
| | Penicillin | >128 | >128 | >128 |
| | Ampicillin | >128 | >128 | 16->128 |
| | Oxacillin | >128 | >128 | >128 |
| | Vancomycin | >128 | >128 | 128->128 |

Embodiment 5

In Vivo Activity of the Novel Antibiotics to Protect Animals Infected by Staphylococcus aureus, Enterococcus faecalis or E. coli 1. Experimental Materials
   (1) Drugs
   The drugs used in this embodiment were same with that used in embodiment 4.
   The above drugs were dissolved and diluted by sterilized water, and the injection concentrations of each drug were 10 mg/kg, 5 mg/kg and 2.5 mg/kg.
   (2) Bacteria
   Methicillin-resistant Staphylococcus aureus ATCC BAA-42, penicillin-resistant Staphylococcus aureus ATCC 29213, vancomycin-resistant Enterococcus faecalis ATCC 700802, E. coli (clinical separated ampicillin sensitive strain, 32033).
2. Experimental Methods
   Kungming mice (n=340), half male and half female, weighing 15-20 g being given intraperitoneal injection of Staphylococcus aureus ATCC BAA-42, ATCC 29213, Enterococcus ATCC 700802 and E. coli (clinical separated ampicillin sensitive strain, 32033) were divided into four groups at random, therein PMC-SA1, penicillin, ampicillin, cefazolin and vancomycin experimental group are set respectively as 5 mice per group, while the control group is set as 10 mice per group. After given intraperitoneal injection of fatal dose of above-mentioned bacteria, the mice of each drug experimental group respectively were given once intravenous injection of the drug by 10 mg, 5 mg, 2.5 mg/kg. The results were observed per 24 hours for 7-14 days. The positive result is mice's death.
3. Results
   The results of 5 mg, 3 mg and 1 mg drug dosage groups showed that in the three dosage groups, the survival rate of mice in PMC-SA1 group always kept constant distance to that of mice in vancomycin group. Indicating the PMC-SA1 has far better treatment effects on anti-methicillin-resistant Staphylococcus aureus infection than vancomycin in vivo. This may be caused by the dual effects of PMC-SA1 sterilizing and controlling bacteria toxin excretion. As a result, the drug may possess treatment effects that other antibiotics haven't on clinical application, while the mortality rate of mice treated by other antibiotics were above 80%, which was no longer comparable to the novel antibiotic. And the mice in control group were all dead in 48 hours.

The experimental results were shown in Table 2.

TABLE 2

The result of PMC-SA1 protection test in vivo (intravenous injection)

| Bacteria (number) amount of infected bacteria (cfu/ml) | Drugs | MIC (μg/ml) | ED$_{50}$ mg/kg | 95% confidence limit (mg/kg) |
|---|---|---|---|---|
| Enterococcus ATCC 700802 (7.0 × 10$^6$) | PMC-SA1 | 16 | 18.2 | 8.90-19.62 |
| | Cefazolin | >128 | >10 | >10 |
| | penicillin | 4 | 4.16 | 3.27-4.86 |
| | ampicillin | 2.5 | 3.00 | 2.87-6.77 |
| | vancomycin | >16 | 3.66 | 3.54-5.41 |
| Staphylococcus aureus MRSA BAA-42 (6.5 × 10$^5$) | PMC-SA1 | 0.5 | 4.12 | 3.82-6.61 |
| | Cefazolin | 6 | 9.04 | 6.84-12.16 |
| | penicillin | 8 | 14.71 | 12.29-21.52 |
| | ampicillin | 16 | 25.41 | 19.43-42.70 |
| | vancomycin | 0.5 | 3.54 | 2.75-6.16 |
| Staphylococcus aureus ATCC 29213 (4.6 × 10$^5$) | PMC-SA1 | 0.5 | 10.35 | 8.74-15.28 |
| | Cefazolin | 7 | 29.11 | 18.42-59.64 |
| | penicillin | 16 | 10.75 | 8.12-17.79 |
| | ampicillin | 1.5 | 14.05 | 9.00-46.51 |
| | vancomycin | 0.5 | 2.42 | 2.71-3.79 |
| E. coli 02-1-65 (3.8 × 10$^5$) | PMC-SA1 | 1 | 3.78 | 3.48-6.08 |
| | Cefazolin | >128 | >30 | >35 |
| | penicillin | >128 | >34.5 | >36 |
| | ampicillin | >128 | >32 | >40.11 |
| | vancomycin | 128 | >40.12 | >44.31 |

According to Table 1 in embodiment 4 and Table 2 in embodiment 5, it could be seen that:

1. Comparison of the in vitro antibacterial activity of Staphylococcus aureus (MRSA): the measured value of oxacillin MIC90 was eight times more than that of PMC-SA1. The molecular weight of PMC-SA1 (700000 daltons) was forty-nine times more than that of vancomycin (1,400 daltons), 155 times more than that of oxacillin (450 daltons). Standardized by the same drug molecular number in unit volume, the in vitro antibacterial activity of PMC-SA1 on Staphylococcus aureus (MRSA) was three times stronger than that of vancomycin to MRSA, and 1,240 times stronger than that of oxacillin to MRSA.

2. In mice in vivo protection experiments, under the condition of minimal dosage (2.5 mg/kg) the mortality rate of PMC-SA1 group was the lowest (40%), the mortality rates of other groups are respectively penicillin group 60%, ampicillin group 100%, vancomycin group 60%, control group 100%. The result shows the protective rate of PMC-SA1 is at the top (60%); while the protective rate of penicillin as well as vancomycin takes the second place (40%).

Embodiment 6

The Effect of the Novel Antibiotics on Growth of Staphylococcus epidermidis

The bacterium is Staphylococcus epidermidis reference culture No. 26069, purchased from China Center of Culture Collection (National Institute for the Control of Pharmaceutical and Biological Products). 3 microliter of bacterium solution ($10^6$ CFU/ml level bacterium amount) was added into 10 ml culture solution containing 1% peptone, 1% NaCl, 0.5% yeast extract, 0.5% glucose and 0.1% $K_2HPO_4$. Totally four groups were prepared. The first group as control was added 0.3M NaCl+50 mM boric acid buffer fluid by the same volume with that of antibiosis polypeptide liquid added in any experimental groups, the second group was added penicillin G sodium by 2 µg/ml, PMC-SA1 and PMC-SE was added in the other experimental groups by 2 µg/ml (0.3 M NaCl+50 mM boric acid buffer fluid was preservative fluid).

Figure 10:
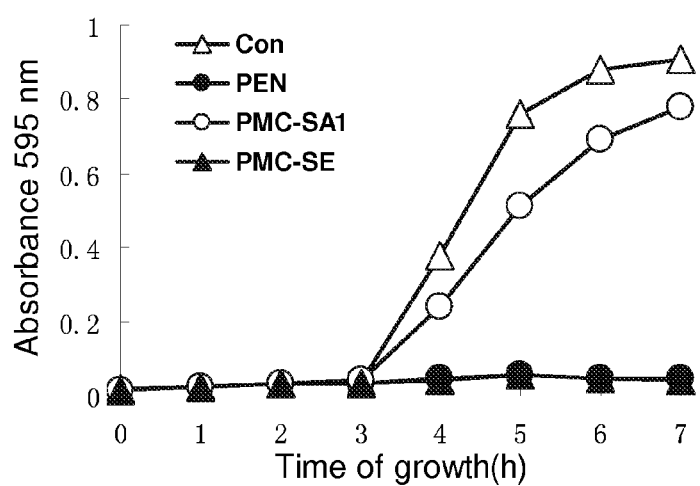
FIG. 10 shows the result of experiment for the bactericidal activity of the novel antibiotic PMC-SA1 and PMC-SE on *Staphylococcus epidermidis*. Wherein the growth of *Staphylococcus epidermidis* can only be partly restrained by PMC-SA1, and completely restrained by PMC-SE. Con means control; PEN means penicillin; PMC means PMC-SA1; PMC-SE means novel antibiotic PMC-SE. The concentration of drugs is 2 µg/ml.

The solution of above groups was put into 100 ml conical flask, 200 rpm, grew at 37° C. 100 µl was sampled per hour, and added onto 96-pore ELISA plate to measure bacteria grown cloudiness by spectrophotometer (A595 nm) color comparison. The bacteria growth curve was drawn up to compare the bacteriostasis efficacy of the novel antibiotics. The result is shown in FIG. 10, the growing of *Staphylococcus epidermidis* can be partly restrained by anti-*Staphylococcus aureus* polypeptide PMC-SA1, and effectively restrained by anti-*Staphylococcus epidermidis* polypeptide PMC-SE.

Embodiment 7

The Comparison of Bacteriostasis Effects of Some of the Novel Antibiotics

The following experiment was set for comparing bacteriostasis effects of 6 kinds of the novel antibiotics. The experimental bacteriaum was United States Standard Strain methicillin-resistant *Staphylococcus aureus* ATCC BAA-42. 5 microliter of bacteria solution ($10^6$ CFU/ml level bacterium amount) was added into 10 ml culture solution containing 1% peptone, 1% NaCl, 0.5% yeast extract, 0.5% glucose and 0.1% $K_2HPO_4$, total of 8 groups were prepared. The first group as control was added 0.3 M NaCl+50 mM boric acid buffer fluid by the same volume as that of antibiosis polypeptide liquid added in any experimental groups, the second group was added penicillin G sodium by 5 µg/ml, PMC-SA1, PMC-SA2, PMC-SA3, PMC-SA4, PMC-SE and PMC-PA were added in the other experimental groups with preservative fluid being 0.3 M NaCl+50 mM boric acid buffer fluid by 5 ug/ml.

Figure 11:
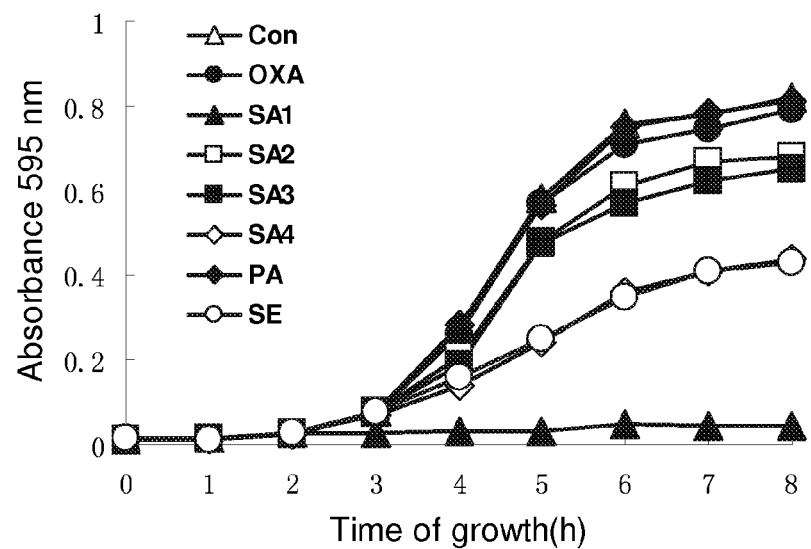
FIG. 11 shows the result of experiment for the bactericidal activity of all sorts of obtained novel antibiotics on methicillin-resistant *Staphylococcus aureus* (ATCC BAA-42). The result shows that growth of methicillin-resistant *Staphylococcus aureus* can hardly be restrained by Oxacillin. The bacteriostasis effect of PMC-PA was the worst, the bacteriostasis effect of PMC-SA1 was the best, that of PMC-SE and PMC-SA4 is less better, while that of PMC-SA2 as well as PMC-SA3 is still less better. Con means control; Oxa means Oxacillin; SA1 means PMC-SA1; SA2 means PMC-SA2; SA3 means PMC-SA3; SA4 means PMC-SA4; SE means PMC-SE and PA means PMC-PA. The concentration of drugs is 5 µg/ml.

The solution of above groups was put into 100 ml conical flask, 200 rpm, grew at 37° C. 100 µl was sampled per hour, and added onto 96-pore ELISA plate and measured bacteria grown cloudiness by spectrophotometer (A595 nm) color comparison. The bacteria growth curve was drawn up to compare the bacteriostasis efficacy of antibiosis polypeptide. The result is shown in FIG. 11.

The result shows that growth of methicillin-resistant *Staphylococcus aureus* can hardly be restrained by oxacillin. The bacteriostasis effect of PMC-PA was the worst, the bacteriostasis effect of PMC-SA1 was the best, that of PMC-SE and PMC-SA4 is less better, while that of PMC-SA2 as well as PMC-SA3 is still less better.

Embodiment 8

The Effect of the Novel Antibiotic to *Pseudomonas aeruginosa*

The experimental bacterium was *Pseudomonas aeruginosa* Standard Strain (ATCC 27853) purchased from the Center for General Microorganism of the Administration (CGMCC). 5 microliter bacteria solution ($10^6$ CFU/ml level bacterium amount) was added into 10 ml MH culture solution. Seven groups are prepared. 0.3 M NaCl+50 mM boric acid buffer fluid which amount was identical to amount of antibiosis polypeptide liquid in the experimental group was added as control in the first group, 5 µg/ml wild-type colicin Ia was added in the second group, 5 µg/ml PMC-SA1 was added in the third group, and 5 µg/ml PMC-PA was added in the fourth group.

Liquid in the above groups was put into 100 ml conical flask, 200 rpm, grew at 37° C. 100 µl was sampled per hour, and added onto 96-hole Elisa Plate to measure bacteria grown cloudiness by spectrophotometer (A595 nm) color comparison. The bacteria growth curve was drawn up to compare the bacteriostasis efficacy of antibiosis polypeptide. The result is shown in FIG. 12.

Figure 12:
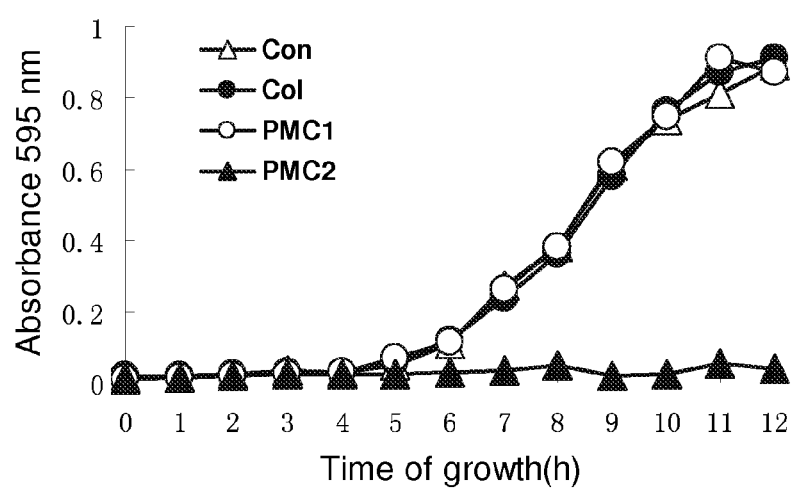
FIG. 12 shows the result of experiment for the bactericidal activity of the novel antibiotic PMC-SA1 and PMC-PA on *Pseudomonas aeruginosa*. Wherein the growth of *Pseudomonas aeruginosa* is completely restrained only by PMC-PA. Con means Control. COL means wild-type colicin. PMC1 means novel antibiotic PMC-SA1. PMC2 means PMC-PA. The concentration of drugs is 5 µg/ml.

It can be seen from FIG. 12, the growth of *Pseudomonas aeruginosa* can be completely restrained by PMC-PA, and can not be effectively restrained by wild-type colicin Ia or PMC-SA1.

Embodiment 9

In Vivo Experiments of the Novel Antibiotics to Protect Animals Infected by Multiple-Drug Resistance *Pseudomonas aeruginosa*

Figure 13:
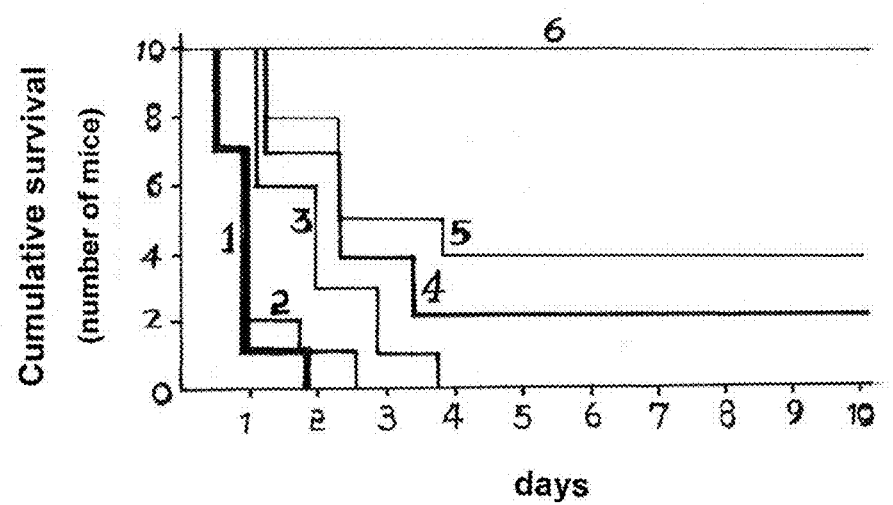
FIG. 13 shows the mice survival curve which was the result of in vivo experiment of the novel antibiotics to protect animals infected by multiple-drug resistance *Pseudomonas aeruginosa*. 1) Control, 2) 50 mg/kg piperacillin group, 3) 15 mg/kg amikacin group, 4) 50 mg/kg ceftazidime group, 5) 5 mg/kg levofloxacin group, 6) 5 mg/kg PMC-PA group.

1. Experimental Materials
   (1) Drugs
   PMC-PA, piperacillin, amikacin, ceftazidime, levofloxacin.
   (2) Bacterium
   Multiple-drug resistance *Pseudomonas aeruginosa* (clinical separated strain 13280, isolated by laboratory bacteria room of West China Hospital)
2. Experimental Methods
   Kungming mice (n=60), half male and half female, weighing 15-20 g were given intraperitoneal injection of multiple-drug resistance *Pseudomonas aeruginosa*, therein PMC-PA, piperacillin, amikacin, ceftazidime and levofloxacin experimental group were set respectively as 10 mice per group, while the control group was set as 10 mice per group. After given intraperitoneal injection of fatal dose of the bacterium, the mice in drug experimental groups respectively were given an intravenous injection of one kind of above drugs, the results were observed per 24 hours for continuous 10 days. The positive result was mouse's death.
3. Results
   As the mice survival curve shown in FIG. 13, after given interaperitonea injection of fatal dose of multiple-drug resistance *Pseudomonas aeruginosa*, (1) mice in control group were all dead in 2 days, (2) mice in 50 mg/kg piperacillin group were all dead in 3 days, (3) mice in 5 mg/kg amikacin 1 group were all dead in 4 days, (4) survival rate of mice in 50 mg/kg ceftazidime group was 20% in 10 days, (5) survival rate of mice in 5 mg/kg levofloxacin group was 40% in 10 days, (6) survival rate of mice in 5 mg/kg PMC-PA group was 100% in 10 days.

The result shows that for mice infected by fatal dose of multiple-drug resistance *Pseudomonas aeruginosa*, the novel antibiotic PMC-PA of the present invention displayed antibacterial activity that traditional antibiotics aren't comparable with.

Embodiment 10

Immunity Effect of the Allosteric Colicin Peptide

Allosteric peptide of Colicin Ia, i.e. Ia', PMC-SA1 obtained in embodiment 1, wild-type colicin Ia and the anti-*Staphylo-* coccus aureus peptide (ZL01128836.1) which invented by the present inventor were taken respectively to immunize mice. After admixturing with the adjuvant, the above proteins were interaperitonea injected respectively to the mice by 50 µg per mouse for one time of foundational quantity and 50 µg per mouse for one time of additional quantity totally 5 times by two weeks interval. Indirect ELISA detection method was applied to detect the valence of mouse sera (Xiao Yi, et. al., Preparation and preliminary characterization of monoclonal antibodies against *Pheromonicin*-and-*Staphylococcus aureus*, Shanxi Medical Journal, 35(1): 6-7, 32 (2006)). The valence of mouse sera which immunized by wild type colicin Ia as well as anti-*Staphylococcus aureus* polypeptide (ZL01128836.1) was $10^{-4}$ to $10^{-5}$, while the valence of mouse sera which immunized by allosteric peptide of colicin Ia and PMC-SA1 was $10^{-2}$ to $10^{-3}$.

Therefore, the possibility of causing host allergic reaction by allosteric peptide of colicin Ia and the novel antibiotic PMC-SA1 in the invention was lower one to two order of magnitude than that of anti-*Staphylococcus aureus* polypeptide.

Those skilled in the art will recognize, or be able to ascertain using no more than routine experimentation, many equivalents to the specific embodiments of the invention described herein. Such equivalents are intended to be encompassed by the following claims.

The invention claimed is:

1. An allosteric colicin being yielded by artificially mutating the amino acid residues G11A, H22R, A26G, V31L and H40K in the peptide chain of wild type Colicin E1, Ia, Ib, A, B, N, or their ion channel-forming structural domain.

2. The allosteric colicin of claim 1 yielded by mutating wild-type Colicin Ia, the allosteric colicin having the amino acid sequence set forth in SEQ ID NO: 36.

3. An isolated nucleotide molecule encoding the peptide of the allosteric colicin of claim 1.

4. The isolated nucleotide molecule of claim 3, having the nucleotide sequence set forth in SEQ ID No.11.

5. A medicament comprising the allosteric colicin of claim 1 and a pharmaceutically acceptable carrier or excipient.

6. An antibiotic comprising:
an allostaeric colicin peptide having an end connected linearly to the end of a peptide of *Staphylococcus aureus* pheromone AgrD I, AgrD II, AgrD III, AgrD IV or *Staphylococcus epidermidis* pheromone.

7. The antibiotic of claim 6, wherein said allosteric colicin is yielded by artificially mutating wildtype Colicin Ia, and linking an N-terminus of any peptide of said *Staphylococcus aureus* pheromone AgrD I, AgrD II, AgrD III, AgrD IV or *Staphylococcus epidermidis* pheromone to a C-terminus of said allosteric colicin peptide of Ia to form the connected peptides with amino acid sequences set forth in SEQ ID No. 13, 15, 17, 19 or 21, respectively.

8. The antibiotic of claim 6, wherein a C-terminus of a *Staphylococcus aureus* pheromone AgrD I is connected to a N-terminus of said allosteric peptide of Ia to form a fusion peptide with amino acid sequence set forth in SEQ ID NO. 23.

9. An isolated nucleotide molecule encoding the antibiotic of claim 6.

10. The isolated nucleotide molecule of claim 9, having a nucleotide sequence set forth in SEQ ID No: 12, 14, 16, 18, 20 or 22.

11. A medicament comprising:
the antibiotic of claim 6 and a pharmaceutically acceptable carrier or excipient.

12. A method of construction of an antibiotic, the method comprising:
obtaining a recombinant plasmid encoding the antibiotic of claim 6;
transfecting the recombinant plasmid into an *E. coli* BL21 expression system to express an allostaeric colicin peptide having an end connected linearly to the end of a peptide of *Staphylococcus aureus* pheromone AgrD I, AgrD II, AgrD III, AgrD IV or *Staphylococcus epidermidis* pheromone; and
separating and purifying the allostaeric colicin peptide to obtain the antibiotic.

13. An isolated nucleotide molecule encoding the peptide of the allosteric colicin of claim 2.

14. An isolated nucleotide molecule encoding the antibiotics of claim 7.

15. An isolated nucleotide molecule encoding the antibiotics of claim 8.

16. A method of construction of an antibiotic, the method comprising:
obtaining a recombinant plasmid having a nucleotide sequence set forth in SEQ ID No: 12, 14, 16, 18, 20 or 22;
transfecting the recombinant plasmid into an *E. coli* BL21 expression system to express an allostaeric colicin peptide having an end connected linearly to the end of a peptide of *Staphylococcus aureus* pheromone AgrD I, AgrD II, AgrD III, AgrD IV or *Staphylococcus epidermidis* pheromone; and
separating and purifying the allostaeric colicin peptide to obtain the antibiotic.

* * * * *

UNITED STATES PATENT AND TRADEMARK OFFICE
CERTIFICATE OF CORRECTION

| | | |
|---|---|---|
| PATENT NO. | : 8,563,503 B2 | Page 1 of 2 |
| APPLICATION NO. | : 13/022512 | |
| DATED | : October 22, 2013 | |
| INVENTOR(S) | : Qiu | |

It is certified that error appears in the above-identified patent and that said Letters Patent is hereby corrected as shown below:

On the title page, Item (56), under "OTHER PUBLICATIONS", in Column 2, Line 1, delete "Qiu et al, Major transmemebrane movement soociated with colicin Ia" and insert -- Qiu et al., Major transmembrane movement associated with colicin Ia --, therefor.

On the title page, Item (56), under "OTHER PUBLICATIONS", in Column 2, Line 3, delete "Ji et al, Cell density control of staphyliccocal" and insert -- Ji et al., Cell density control of staphylococcal --, therefor.

In the Specification

In Column 1, Line 33, delete "transmemebrane" and insert -- transmembrane --, therefor.

In Column 1, Line 44, delete "staphyliccocal" and insert -- staphylococcal --, therefor.

In Column 3, Line 8, delete "target pathogen pathogen" and insert -- target pathogen --, therefor.

In Column 3, Line 21, delete "Stapylococcus" and insert -- Staphylococcus --, therefor.

In Column 3, Line 41, delete "Stapylococcus" and insert -- Staphylococcus --, therefor.

In Column 3, Line 48, delete "Stapylococcus" and insert -- Staphylococcus --, therefor.

In Column 6, Line 5, delete "Stapylococcus" and insert -- Staphylococcus --, therefor.

In Column 13, Line 31, delete "bacteriaum" and insert -- bacterium --, therefor.

Signed and Sealed this
Tenth Day of June, 2014

Michelle K. Lee
*Deputy Director of the United States Patent and Trademark Office*

CERTIFICATE OF CORRECTION (continued)
U.S. Pat. No. 8,563,503 B2

In the Claims

In Column 59, Line 15, in Claim 6, delete "allostaeric" and insert -- allosteric --, therefor.

In Column 60, Line 10, in Claim 12, delete "allostaeric" and insert -- allosteric --, therefor.

In Column 60, Line 15, in Claim 12, delete "allostaeric" and insert -- allosteric --, therefor.

In Column 60, Line 28, in Claim 16, delete "allostaeric" and insert -- allosteric --, therefor.

In Column 60, Line 33, in Claim 16, delete "allostaeric" and insert -- allosteric --, therefor.

SEQUENCE LISTING

<160> NUMBER OF SEQ ID NOS: 37

<210> SEQ ID NO 1
<211> LENGTH: 24
<212> TYPE: DNA
<213> ORGANISM: Staphylococcus aureus
<220> FEATURE:
<223> OTHER INFORMATION: Gene encoding AgrDI

<400> SEQUENCE: 1
tattccacct gtgattttat aatg                                          24

<210> SEQ ID NO 2
<211> LENGTH: 8
<212> TYPE: PRT
<213> ORGANISM: Staphylococcus aureu
<220> FEATURE:
<223> OTHER INFORMATION: peptide of AgrDI

<400> SEQUENCE: 2

Tyr Ser Thr Cys Asp Phe Ile Met
1               5

<210> SEQ ID NO 3
<211> LENGTH: 27
<212> TYPE: DNA
<213> ORGANISM: Staphylococcus aureu
<220> FEATURE:
<223> OTHER INFORMATION: Gene encoding AgrDII

<400> SEQUENCE: 3
ggagttaacg catgttcttc cctgttt                                       27

<210> SEQ ID NO 4
<211> LENGTH: 9
<212> TYPE: PRT
<213> ORGANISM: Staphylococcus aureu
<220> FEATURE:
<223> OTHER INFORMATION: Peptide of AgrDII

<400> SEQUENCE: 4

Gly Val Asn Ala Cys Ser Ser Leu Phe
1               5

<210> SEQ ID NO 5
<211> LENGTH: 24
<212> TYPE: DNA
<213> ORGANISM: Staphylococcus aureu
<220> FEATURE:
<223> OTHER INFORMATION: Gene encoding AgrD III

<400> SEQUENCE: 5

-continued

```
tatataaact gtgatttct tctg                                              24

<210> SEQ ID NO 6
<211> LENGTH: 8
<212> TYPE: PRT
<213> ORGANISM: Staphylococcus aureu
<220> FEATURE:
<223> OTHER INFORMATION: Peptide of AgrD III

<400> SEQUENCE: 6

Tyr Ile Asn Cys Asp Phe Leu Leu
1               5

<210> SEQ ID NO 7
<211> LENGTH: 24
<212> TYPE: DNA
<213> ORGANISM: Staphylococcus aureu
<220> FEATURE:
<223> OTHER INFORMATION: Gene encoding AgrD IV

<400> SEQUENCE: 7
tattccacct gttactttat aatg                                              24

<210> SEQ ID NO 8
<211> LENGTH: 8
<212> TYPE: PRT
<213> ORGANISM: Staphylococcus aureu
<220> FEATURE:
<223> OTHER INFORMATION: Peptide of AgrD IV

<400> SEQUENCE: 8

Tyr Ser Thr Cys Tyr Phe Ile Met
1               5

<210> SEQ ID NO 9
<211> LENGTH: 24
<212> TYPE: DNA
<213> ORGANISM: Staphylococcus epidermidis
<220> FEATURE:
<223> OTHER INFORMATION: Gene encoding Staphylococcus epidermidis
      pheromone

<400> SEQUENCE: 9
gattccgttt gtgcatccta tttt                                              24

<210> SEQ ID NO 10
<211> LENGTH: 8
<212> TYPE: PRT
<213> ORGANISM: Staphylococcus epidermidis
<220> FEATURE:
<223> OTHER INFORMATION: Peptide of Staphylococcus epidermidis pheromone

<400> SEQUENCE: 10

Asp Ser Val Cys Ala Ser Tyr Phe
1               5

<210> SEQ ID NO 11
<211> LENGTH: 1878
<212> TYPE: DNA
<213> ORGANISM: Escherichia coli
<220> FEATURE:
<223> OTHER INFORMATION: The gene of colicin Ia'

<400> SEQUENCE: 11
atgtctgacc ctgtacgtat tacaaatccc gcagcagaat cgctggggta tgattcagat      60
ggcaaagaaa ttatgggtgt tgatatttat ctcaaccctc cacgtgtcga tgtctttaaa     120
```

```
ggtaccccgc ctgcatggag ttccttcggg aacaaaacca tctggggcgg aaacgagtgg      180
gttgatgatt ccccaacccg aagtgatatc gaaaaaaggg acaaggaaat cacagcgtac      240
aaaaacacgc tcagcgcgca gcagaaagag aatgagaata agcgtactga agccggaaaa     300
cgcctctctg cggcgattgc tgcaagggaa aaagatgaaa acacactgaa aacactccgt      360
gccggaaacg cagatgccgc tgatattaca cgacaggagt tcagactcct gcaggcagag      420
ctgagagaat acggattccg tactgaaatc gccggatatg acgccctccg gctgcataca      480
gagagccgga tgctgtttgc tgatgctgat tctcttcgta tatctccccg ggaggccagg      540
tcgttaatcg aacaggctga aaacggcag aaggatgcgc agaacgcaga caagaaggcc      600
gctgatatgc ttgctgaata cgagcgcaga aaagtattc tggacacccg gttgtcagag      660
ctggaaaaaa atggcggggc agcccttgcc gttcttgatg cacaacaggc ccgtctgctc      720
gggcagcaga cacggaatga cagggccatt tcagaggccc ggaataaact cagttcagtg      780
acggaatcgc ttaacacggc ccgtaatgca ttaaccagag ctgaacaaca gctgacgcaa      840
cagaaaaaca cgcctgacgg caaaacgata gtttcccctg aaaaattccc ggggcgttca      900
tcaacaaatc attctattgt tgtgagcggt gatccgagat ttgccggtac gataaaaatc      960
acaaccagcg cagtcatcga taaccgtgca aacctgaatt atcttctgag ccattccggt     1020
ctggactata aacgcaatat tctgaatgac cggaatccgg tggtgacaga ggatgtggaa     1080
ggtgacaaga aaatttataa tgctgaagtt gctgaatggg ataagttacg gcaaagattg     1140
cttgatgcca gaaataaaat cacctctgct gaatctgcgg taaattcggc gagaaataac     1200
ctcagtgcca gaacaaatga gcaaaagcat gcaaatgacg ctcttaatgc cctgttgaag     1260
gaaaaagaga atatacgtaa ccagctttcc ggcatcaatc agaagatagc ggaagagaaa     1320
agaaaacagg atgaactgaa ggcaacgaaa gacgcaatta atttcacaac agagttcctg     1380
aaatcagttt cagaaaaata tggtgcaaaa gctgagcagt tagccagaga gatggccggg     1440
caggctaaag ggaagaaaat acgtaatgtt gaagaggcat taaaaacgta tgaaaagtac     1500
cgggctgaca ttaacaaaaa aattaatgca aagatcgtg cagcgattgc cgcagcccct     1560
gagtctgtga agctgtctga tatatcgtct aatctgaaca gattcagtcg gggactggga     1620
tatgcaggaa aatttacaag tcttgctgac tggatcactg agttggtaa ggctgtccgg     1680
acagagaact ggcgtcctct ttttgttaaa acagaaacca tcatagcagg caatgccgca     1740
acggctcttg tggcactggt cttcagtatt cttaccggaa gcgctttagg cattatcggg     1800
tatggttac tgatggctgt caccggtgcg ctgattgatg aatcgcttgt ggaaaaagcg     1860
aataagttct ggggtatt                                                  1878
```

<210> SEQ ID NO 12
<211> LENGTH: 1902
<212> TYPE: DNA
<213> ORGANISM: Artificial Sequence
<220> FEATURE:
<223> OTHER INFORMATION: Gene encoding the novel antibiotic PMC-SA1

<400> SEQUENCE: 12

```
atgtctgacc ctgtacgtat tacaaatccc gcagcagaat cgctggggta tgattcagat       60
ggcaaagaaa ttatgggtgt tgatatttat ctcaaccctc cacgtgtcga tgtctttaaa      120
ggtaccccgc ctgcatggag ttccttcggg aacaaaacca tctggggcgg aaacgagtgg      180
gttgatgatt ccccaacccg aagtgatatc gaaaaaaggg acaaggaaat cacagcgtac      240
aaaaacacgc tcagcgcgca gcagaaagag aatgagaata agcgtactga agccggaaaa     300
```

-continued

```
cgcctctctg cggcgattgc tgcaagggaa aaagatgaaa acacactgaa aacactccgt      360
gccggaaacg cagatgccgc tgatattaca cgacaggagt tcagactcct gcaggcagag      420
ctgagagaat acggattccg tactgaaatc gccggatatg acgccctccg gctgcataca      480
gagagccgga tgctgtttgc tgatgctgat tctcttcgta tatctccccg ggaggccagg      540
tcgttaatcg aacaggctga aaaacggcag aaggatgcgc agaacgcaga caagaaggcc      600
gctgatatgc ttgctgaata cgagcgcaga aaaggtattc tggacacccg gttgtcagag      660
ctggaaaaaa atggcggggc agcccttgcc gttcttgatg cacaacaggc ccgtctgctc      720
gggcagcaga cacggaatga cagggccatt tcagaggccc ggaataaact cagttcagtg      780
acggaatcgc ttaacacggc ccgtaatgca ttaaccagag ctgaacaaca gctgacgcaa      840
cagaaaaaca cgcctgacgg caaaacgata gtttcccctg aaaaattccc ggggcgttca      900
tcaacaaatc attctattgt tgtgagcggt gatccgagat tgccggtac gataaaaatc       960 acaaccagcg cagtcatcga taaccgtgca aacctgaatt atcttctgag ccattccggt     1020
ctggactata acgcaatatt tctgaatgac cggaatccgg tggtgacaga ggatgtggaa     1080
ggtgacaaga aaattataa tgctgaagtt gctgaatggg ataagttacg gcaaagattg      1140
cttgatgcca gaaataaat cacctctgct gaatctgcgg taaattcggc gagaaataac       1200
ctcagtgcca gaacaaatga gcaaaagcat gcaaatgacg ctcttaatgc cctgttgaag     1260 gaaaagaga atatacgtaa ccagctttcc ggcatcaatc agaagatagc ggaagagaaa      1320
agaaaacagg atgaactgaa ggcaacgaaa gacgcaatta atttcacaac agagttcctg     1380
aaatcagttt cagaaaaata tggtgcaaaa gctgagcagt tagccagaga gatggccggg    1440
caggctaaag ggaagaaaat acgtaatgtt gaagaggcat taaaaacgta tgaaaagtac     1500
cgggctgaca ttaacaaaaa aattaatgca aaagatcgtg cagcgattgc cgcagcccctt   1560 gagtctgtga agctgtctga tatatcgtct aatctgaaca gattcagtcg gggactggga    1620
tatgcaggaa aatttacaag tcttgctgac tggatcactg agtttggtaa ggctgtccgg    1680
acagagaact ggcgtcctct ttttgttaaa acagaaacca tcatagcagg caatgccgca    1740
acggctcttg tggcactggt cttcagtatt cttaccggaa gcgctttagg cattatcggg    1800 tatggttta ctgatggctgt caccggtgcg ctgattgatg aatcgcttgt ggaaaaagcg     1860
aataagttct ggggttattc cacctgtgat tttataatga tt                       1902
```

<210> SEQ ID NO 13
<211> LENGTH: 633
<212> TYPE: PRT
<213> ORGANISM: Artificial Sequence
<220> FEATURE:
<223> OTHER INFORMATION: The peptide of PMC-SA1

<400> SEQUENCE: 13

Ser Asp Pro Val Arg Ile Thr Asn Pro Ala Ala Glu Ser Leu Gly Tyr
1               5                   10                  15

Asp Ser Asp Gly Arg Glu Ile Met Gly Val Asp Ile Tyr Leu Asn Pro
            20                  25                  30

Pro Arg Val Asp Val Phe Lys Gly Thr Pro Pro Ala Trp Ser Ser Phe
        35                  40                  45

Gly Asn Lys Thr Ile Trp Gly Gly Asn Glu Trp Val Asp Asp Ser Pro
    50                  55                  60

Thr Arg Ser Asp Ile Glu Lys Arg Asp Lys Glu Ile Thr Ala Tyr Lys
65                  70                  75                  80

```
Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
            115                 120                 125

Thr Arg Gln Glu Phe Arg Leu Leu Gln Ala Glu Leu Arg Glu Tyr Gly
        130                 135                 140

Phe Arg Thr Glu Ile Ala Gly Tyr Asp Ala Leu Arg Leu His Thr Glu
145                 150                 155                 160

Ser Arg Met Leu Phe Ala Asp Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
            195                 200                 205

Arg Lys Gly Ile Leu Asp Thr Arg Leu Ser Glu Leu Glu Lys Asn Gly
        210                 215                 220

Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
                245                 250                 255

Ser Ser Val Thr Glu Ser Leu Asn Thr Ala Arg Asn Ala Leu Thr Arg
            260                 265                 270

Ala Glu Gln Gln Leu Thr Gln Gln Lys Asn Thr Pro Asp Gly Lys Thr
            275                 280                 285

Ile Val Ser Pro Glu Lys Phe Pro Gly Arg Ser Ser Thr Asn His Ser
        290                 295                 300

Ile Val Val Ser Gly Asp Pro Arg Phe Ala Gly Thr Ile Lys Ile Thr
305                 310                 315                 320

Thr Ser Ala Val Ile Asp Asn Arg Ala Asn Leu Asn Tyr Leu Leu Ser
                325                 330                 335

His Ser Gly Leu Asp Tyr Lys Arg Asn Ile Leu Asn Asp Arg Asn Pro
            340                 345                 350

Val Val Thr Glu Asp Val Glu Gly Asp Lys Lys Ile Tyr Asn Ala Glu
            355                 360                 365

Val Ala Glu Trp Asp Lys Leu Arg Gln Arg Leu Leu Asp Ala Arg Asn
        370                 375                 380

Lys Ile Thr Ser Ala Glu Ser Ala Val Asn Ala Arg Asn Asn Leu
385                 390                 395                 400

Ser Ala Arg Thr Asn Glu Gln Lys His Ala Asn Asp Ala Leu Asn Ala
                405                 410                 415

Leu Leu Lys Glu Lys Glu Asn Ile Arg Asn Gln Leu Ser Gly Ile Asn
            420                 425                 430

Gln Lys Ile Ala Glu Glu Lys Arg Lys Gln Asp Glu Leu Lys Ala Thr
            435                 440                 445

Lys Asp Ala Ile Asn Phe Thr Thr Glu Phe Leu Lys Ser Val Ser Glu
        450                 455                 460

Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
                485                 490                 495

Glu Lys Tyr Arg Ala Asp Ile Asn Lys Lys Ile Asn Ala Lys Asp Arg
            500                 505                 510
```

```
Ala Ala Ile Ala Ala Ala Leu Glu Ser Val Lys Leu Ser Asp Ile Ser
            515                 520                 525

Ser Asn Leu Asn Arg Phe Ser Arg Gly Leu Gly Tyr Ala Gly Lys Phe
        530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
                565                 570                 575

Asn Ala Ala Thr Ala Leu Val Ala Leu Val Phe Ser Ile Leu Thr Gly
            580                 585                 590

Ser Ala Leu Gly Ile Ile Gly Tyr Gly Leu Leu Met Ala Val Thr Gly
        595                 600                 605

Ala Leu Ile Asp Glu Ser Leu Val Glu Lys Ala Asn Lys Phe Trp Gly
            610                 615                 620

Ile Tyr Ser Thr Cys Asp Phe Ile Met
625                 630
```

<210> SEQ ID NO 14
<211> LENGTH: 1905
<212> TYPE: DNA
<213> ORGANISM: Artificial Sequence
<220> FEATURE:
<223> OTHER INFORMATION: Gene encoding the novel antibiotic PMC-SA2

<400> SEQUENCE: 14

```
atgtctgacc ctgtacgtat tacaaatccc gcagcagaat cgctggggta tgattcagat      60
ggcaaagaaa ttatggccgt tgatatttat ctcaaccctc cacgtgtcga tgtctttaaa     120
ggtaccccgc tgcatggag ttccttcggg aacaaaacca tctggggcgg aaacgagtgg     180
gttgatgatt ccccaacccg aagtgatatc gaaaaaaggg acaaggaaat cacagcgtac     240
aaaaacacgc tcagcgcgca gcagaaagag aatgagaata gcgtactga agccggaaaa     300
cgcctctctg cggcgattgc tgcaagggaa aaagatgaaa cacactgaa aacactccgt     360
gccggaaacg cagatgccgc tgatattaca cgacaggagt tcagactcct gcaggcagag     420
ctgagagaat acggattccg tactgaaatc gccggatatg acgccctccg gctgcataca     480
gagagccgga tgctgtttgc tgatgctgat tctcttcgta tatctccccg ggaggccagg     540
tcgttaatcg aacaggctga aaacggcag aaggatgcgc agaacgcaga caagaaggcc     600
gctgatatgc ttgctgaata cgagcgcaga aaaggtattc tggacacccg gttgtcagag     660
ctggaaaaaa atggcgggc agcccttgcc gttcttgatg cacaacaggc ccgtctgctc     720
gggcagcaga cacggaatga cagggccatt tcagaggccc ggaataaaact cagttcagtg     780
acggaatcgc ttaacacggc ccgtaatgca ttaaccagag ctgaacaaca gctgacgcaa     840
cagaaaaaca cgcctgacgg caaaacgata gtttcccctg aaaaattccc ggggcgttca     900
tcaacaaatc attctattgt tgtgagcggt gatccgagat ttgccggtac gataaaaatc     960
acaaccagcg cagtcatcga taaccgtgca aacctgaatt atcttctgag ccattccggt    1020
ctggactata aacgcaatat tctgaatgac cggaatccgg tggtgacaga ggatgtggaa    1080
ggtgacaaga aaatttataa tgctgaagtt gctgaatggg ataagttacg gcaaagattg    1140
cttgatgcca gaaataaaat cacctctgct gaatctgcgg taaattcggc gagaaataac    1200
ctcagtgcca gaacaaatga gcaaagcat gcaaatgacg ctcttaatgc cctgttgaag    1260
gaaaagagaa atatacgtaa ccagcttcc ggcatcaatc agaagatagc ggaagagaaa    1320
agaaaacagg atgaactgaa ggcaacgaaa gacgcaatta atttcacaac agagttcctg    1380
```

-continued

```
aaatcagttt cagaaaaata tggtgcaaaa gctgagcagt tagccagaga gatggccggg    1440
caggctaaag ggaagaaaat acgtaatgtt gaagaggcat taaaaacgta tgaaaagtac    1500
cgggctgaca ttaacaaaaa aattaatgca aaagatcgtg cagcgattgc cgcagcccct    1560
gagtctgtga agctgtctga tatatcgtct aatctgaaca gattcagtcg gggactggga    1620
tatgcaggaa aatttacaag tcttgctgac tggatcactg agtttggtaa ggctgtccgg    1680
acagagaact ggcgtcctct ttttgttaaa acagaaacca tcatagcagg caatgccgca    1740
acggctcttg tggcactggt cttcagtatt cttaccggaa gcgctttagg cattatcggg    1800
tatggtttac tgatggctgt caccggtgcg ctgattgatg aatcgcttgt ggaaaaagcg    1860
aataagttct ggggtggagt taacgcatgt tcttccctgt tttaa                    1905
```

<210> SEQ ID NO 15
<211> LENGTH: 634
<212> TYPE: PRT
<213> ORGANISM: ARtificial Sequence
<220> FEATURE:
<223> OTHER INFORMATION: The peptide of PMC-SA2

<400> SEQUENCE: 15

```
Ser Asp Pro Val Arg Ile Thr Asn Pro Ala Glu Ser Leu Gly Tyr
1               5                   10                  15

Asp Ser Asp Gly Arg Glu Ile Met Ala Val Asp Ile Tyr Leu Asn Pro
            20                  25                  30

Pro Arg Val Asp Val Phe Lys Gly Thr Pro Pro Ala Trp Ser Ser Phe
        35                  40                  45

Gly Asn Lys Thr Ile Trp Gly Gly Asn Glu Trp Val Asp Asp Ser Pro
    50                  55                  60

Thr Arg Ser Asp Ile Glu Lys Arg Asp Lys Glu Ile Thr Ala Tyr Lys
65                  70                  75                  80

Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
        115                 120                 125

Thr Arg Gln Glu Phe Arg Leu Leu Gln Ala Glu Leu Arg Glu Tyr Gly
    130                 135                 140

Phe Arg Thr Glu Ile Ala Gly Tyr Asp Ala Leu Arg Leu His Thr Glu
145                 150                 155                 160

Ser Arg Met Leu Phe Ala Asp Ala Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
        195                 200                 205

Arg Lys Gly Ile Leu Asp Thr Arg Leu Ser Glu Leu Glu Lys Asn Gly
    210                 215                 220

Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
                245                 250                 255

Ser Ser Val Thr Glu Ser Leu Asn Thr Ala Arg Asn Ala Leu Thr Arg
            260                 265                 270
```

```
Ala Glu Gln Gln Leu Thr Gln Gln Lys Asn Thr Pro Asp Gly Lys Thr
        275                 280                 285

Ile Val Ser Pro Glu Lys Phe Pro Gly Arg Ser Ser Thr Asn His Ser
    290                 295                 300

Ile Val Val Ser Gly Asp Pro Arg Phe Ala Gly Thr Ile Lys Ile Thr
305                 310                 315                 320

Thr Ser Ala Val Ile Asp Asn Arg Ala Asn Leu Asn Tyr Leu Leu Ser
                325                 330                 335

His Ser Gly Leu Asp Tyr Lys Arg Asn Ile Leu Asn Asp Arg Asn Pro
            340                 345                 350

Val Val Thr Glu Asp Val Glu Gly Asp Lys Lys Ile Tyr Asn Ala Glu
        355                 360                 365

Val Ala Glu Trp Asp Lys Leu Arg Gln Arg Leu Leu Asp Ala Arg Asn
    370                 375                 380

Lys Ile Thr Ser Ala Glu Ser Ala Val Asn Ser Ala Arg Asn Asn Leu
385                 390                 395                 400

Ser Ala Arg Thr Asn Glu Gln Lys His Ala Asn Asp Ala Leu Asn Ala
                405                 410                 415

Leu Leu Lys Glu Lys Glu Asn Ile Arg Asn Gln Leu Ser Gly Ile Asn
            420                 425                 430

Gln Lys Ile Ala Glu Glu Lys Arg Lys Gln Asp Glu Leu Lys Ala Thr
        435                 440                 445

Lys Asp Ala Ile Asn Phe Thr Thr Glu Phe Leu Lys Ser Val Ser Glu
    450                 455                 460

Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
                485                 490                 495

Glu Lys Tyr Arg Ala Asp Ile Asn Lys Lys Ile Asn Ala Lys Asp Arg
            500                 505                 510

Ala Ala Ile Ala Ala Ala Leu Glu Ser Val Lys Leu Ser Asp Ile Ser
        515                 520                 525

Ser Asn Leu Asn Arg Phe Ser Arg Gly Leu Gly Tyr Ala Gly Lys Phe
    530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
                565                 570                 575

Asn Ala Ala Thr Ala Leu Val Ala Leu Val Phe Ser Ile Leu Thr Gly
            580                 585                 590

Ser Ala Leu Gly Ile Ile Gly Tyr Gly Leu Leu Met Ala Val Thr Gly
        595                 600                 605

Ala Leu Ile Asp Glu Ser Leu Val Glu Lys Ala Asn Lys Phe Trp Gly
    610                 615                 620

Ile Gly Val Asn Ala Cys Ser Ser Leu Phe
625                 630

<210> SEQ ID NO 16
<211> LENGTH: 1905
<212> TYPE: DNA
<213> ORGANISM: Artificial Sequence
<220> FEATURE:
<223> OTHER INFORMATION: Gene encoding the novel antibiotic PMC-SA3

<400> SEQUENCE: 16
atgtctgacc ctgtacgtat tacaaatccc gcagcagaat cgctggggta tgattcagat      60
```

```
ggcaaagaaa ttatggccgt tgatatttat ctcaacccct cacgtgtcga tgtctttaaa      120
ggtaccccgc ctgcatggag ttccttcggg aacaaaacca tctggggcgg aaacgagtgg      180
gttgatgatt ccccaacccg aagtgatatc gaaaaaggg acaaggaaat cacagcgtac       240
aaaaacacgc tcagcgcgca gcagaaagag aatgagaata agcgtactga agccggaaaa      300
cgcctctctg cggcgattgc tgcaaggaa aaagatgaaa acacactgaa acactccgt        360 gccggaaacg cagatgccgc tgatattaca cgacaggagt tcagactcct gcaggcagag      420
ctgagagaat acggattccg tactgaaatc gccggatatg acgccctccg gctgcataca      480
gagagccgga tgctgtttgc tgatgctgat tctcttcgta tatctccccg ggaggccagg      540
tcgttaatcg aacaggctga aaaacggcag aaggatgcgc agaacgcaga caagaaggcc      600
gctgatatgc ttgctgaata cgagcgcaga aaaggtattc tggacacccg gttgtcagag      660
ctggaaaaaa atggcggggc agcccttgcc gttcttgatg cacaacaggc ccgtctgctc      720
gggcagcaga cacggaatga cagggccatt tcagaggccc ggaataaaact cagttcagtg    780 acggaatcgc ttaacacggc ccgtaatgca ttaaccagag ctgaacaaca gctgacgcaa      840
cagaaaaaca cgcctgacgg caaaacgata gtttcccctg aaaaattccc ggggcgttca     900
tcaacaaatc attctattgt tgtgagcggt gatccgagat tgccggtac gataaaaatc      960 acaaccagcg cagtcatcga taaccgtgca aacctgaatt atcttctgag ccattccggt     1020
ctggactata aacgcaatat tctgaatgac cggaatccgg tggtgacaga ggatgtggaa     1080
ggtgacaaga aaatttataa tgctgaagtt gctgaatggg ataagttacg gcaaagattg     1140
cttgatgcca gaaataaaat cacctctgct gaatctgcgg taaattcggc gagaaataac     1200
ctcagtgcca gaacaaatga gcaaaagcat gcaaatgacg ctcttaatgc cctgttgaag     1260
gaaaagagaa atatacgtaa ccagctttcc ggcatcaatc agaagatagc ggaagagaaa     1320
agaaaacagg atgaactgaa ggcaacgaaa gacgcaatta atttcacaac agagttcctg     1380
aaatcagttt cagaaaaata tggtgcaaaa gctgagcagt tagccagaga gatggccggg     1440
caggctaaag ggaagaaaat acgtaatgtt gaagaggcat taaaaacgta tgaaaagtac     1500
cgggctgaca ttaacaaaaa aattaatgca aaagatcgtg cagcgattgc cgcagcccctt    1560 gagtctgtga agctgtctga tatatcgtct aatctgaaca gattcagtcg gggactggga     1620
tatgcaggaa aatttacaag tcttgctgac tggatcactg agtttggtaa ggctgtccgg     1680
acagagaact ggcgtcctct ttttgttaaa acagaaacca tcatagcagg caatgccgca     1740
acggctcttg tggcactggt cttcagtatt cttaccggaa gcgctttagg cattatcggg     1800
tatggtttac tgatggctgt caccggtgcg ctgattgatg aatcgcttgt ggaaaaagcg     1860
aataagttct gggtattta tataaactgt gatttcttc tgtaa                       1905
```

<210> SEQ ID NO 17
<211> LENGTH: 633
<212> TYPE: PRT
<213> ORGANISM: Artificial Sequence
<220> FEATURE:
<223> OTHER INFORMATION: The peptide of PMC-SA3

<400> SEQUENCE: 17

Ser Asp Pro Val Arg Ile Thr Asn Pro Ala Ala Glu Ser Leu Gly Tyr
1               5                   10                  15

Asp Ser Asp Gly Arg Glu Ile Met Gly Val Asp Ile Tyr Leu Asn Pro
            20                  25                  30

Pro Arg Val Asp Val Phe Lys Gly Thr Pro Pro Ala Trp Ser Ser Phe

-continued

```
            35                  40                  45
Gly Asn Lys Thr Ile Trp Gly Gly Asn Glu Trp Val Asp Asp Ser Pro
 50                  55                  60
Thr Arg Ser Asp Ile Glu Lys Arg Asp Lys Glu Ile Thr Ala Tyr Lys
 65                  70                  75                  80
Asn Thr Leu Ser Ala Gln Gln Lys Glu Asn Glu Asn Lys Arg Thr Glu
                 85                  90                  95
Ala Gly Lys Arg Leu Ser Ala Ala Ile Ala Ala Arg Glu Lys Asp Glu
                100                 105                 110
Asn Thr Leu Lys Thr Leu Arg Ala Gly Asn Ala Asp Ala Ala Asp Ile
                115                 120                 125
Thr Arg Gln Glu Phe Arg Leu Leu Gln Ala Glu Leu Arg Glu Tyr Gly
130                 135                 140
Phe Arg Thr Glu Ile Ala Gly Tyr Asp Ala Leu Arg Leu His Thr Glu
145                 150                 155                 160
Ser Arg Met Leu Phe Ala Asp Ala Asp Ser Leu Arg Ile Ser Pro Arg
                165                 170                 175
Glu Ala Arg Ser Leu Ile Glu Gln Ala Glu Lys Arg Gln Lys Asp Ala
                180                 185                 190
Gln Asn Ala Asp Lys Lys Ala Ala Asp Met Leu Ala Glu Tyr Glu Arg
                195                 200                 205
Arg Lys Gly Ile Leu Asp Thr Arg Leu Ser Glu Leu Glu Lys Asn Gly
                210                 215                 220
Gly Ala Ala Leu Ala Val Leu Asp Ala Gln Gln Ala Arg Leu Leu Gly
225                 230                 235                 240
Gln Gln Thr Arg Asn Asp Arg Ala Ile Ser Glu Ala Arg Asn Lys Leu
                245                 250                 255
Ser Ser Val Thr Glu Ser Leu Asn Thr Ala Arg Asn Ala Leu Thr Arg
                260                 265                 270
Ala Glu Gln Gln Leu Thr Gln Gln Lys Asn Thr Pro Asp Gly Lys Thr
                275                 280                 285
Ile Val Ser Pro Glu Lys Phe Pro Gly Arg Ser Ser Thr Asn His Ser
290                 295                 300
Ile Val Val Ser Gly Asp Pro Arg Phe Ala Gly Thr Ile Lys Ile Thr
305                 310                 315                 320
Thr Ser Ala Val Ile Asp Asn Arg Ala Asn Leu Asn Tyr Leu Leu Ser
                325                 330                 335
His Ser Gly Leu Asp Tyr Lys Arg Asn Ile Leu Asn Asp Arg Asn Pro
                340                 345                 350
Val Val Thr Glu Asp Val Glu Gly Asp Lys Lys Ile Tyr Asn Ala Glu
                355                 360                 365
Val Ala Glu Trp Asp Lys Leu Arg Gln Arg Leu Leu Asp Ala Arg Asn
                370                 375                 380
Lys Ile Thr Ser Ala Glu Ser Val Asn Ser Ala Arg Asn Asn Leu
385                 390                 395                 400
Ser Ala Arg Thr Asn Glu Gln Lys His Ala Asn Asp Ala Leu Asn Ala
                405                 410                 415
Leu Leu Lys Glu Lys Glu Asn Ile Arg Asn Gln Leu Ser Gly Ile Asn
                420                 425                 430
Gln Lys Ile Ala Glu Glu Lys Arg Lys Gln Asp Glu Leu Lys Ala Thr
                435                 440                 445
Lys Asp Ala Ile Asn Phe Thr Thr Glu Phe Leu Lys Ser Val Ser Glu
450                 455                 460
```

```
Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
                485                 490                 495

Glu Lys Tyr Arg Ala Asp Ile Asn Lys Lys Ile Asn Ala Lys Asp Arg
            500                 505                 510

Ala Ala Ile Ala Ala Leu Glu Ser Val Lys Leu Ser Asp Ile Ser
            515                 520                 525

Ser Asn Leu Asn Arg Phe Ser Arg Gly Leu Gly Tyr Ala Gly Lys Phe
        530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
                565                 570                 575

Asn Ala Ala Thr Ala Leu Val Ala Leu Val Phe Ser Ile Leu Thr Gly
            580                 585                 590

Ser Ala Leu Gly Ile Ile Gly Tyr Gly Leu Leu Met Ala Val Thr Gly
        595                 600                 605

Ala Leu Ile Asp Glu Ser Leu Val Glu Lys Ala Asn Lys Phe Trp Gly
610                 615                 620

Ile Tyr Ile Asn Cys Asp Phe Leu Leu
625                 630

<210> SEQ ID NO 18
<211> LENGTH: 1902
<212> TYPE: DNA
<213> ORGANISM: Artificial Sequence
<220> FEATURE:
<223> OTHER INFORMATION: Gene encoding the novel antibiotic PMC-SA4

<400> SEQUENCE: 18
atgtctgacc ctgtacgtat tacaaatccc gcagcagaat cgctggggta tgattcagat      60
ggcaaagaaa ttatgggtgt tgatatttat ctcaaccctc cacgtgtcga tgtctttaaa     120
ggtaccccgc ctgcatggag ttccttcggg aacaaaacca tctggggcgg aaacgagtgg     180
gttgatgatt ccccaacccg aagtgatatc gaaaaaaggg acaaggaaat cacagcgtac     240
aaaaacacgc tcagcgcgca gcagaaagag aatgagaata gcgtactga agccggaaaa     300 cgcctctctg cggcgattgc tgcaagggaa aaagatgaaa acacactgaa aacactccgt     360
gccggaaacg cagatgccgc tgatattaca cgacaggagt tcagactcct gcaggcagag     420
ctgagagaat acggattccg tactgaaatc gccggatatg acgccctccg gctgcataca     480
gagagccgga tgctgttttgc tgatgctgat tctcttcgta tatctccccg ggaggccagg     540
tcgttaatcg aacaggctga aaacggcag aaggatgcgc agaacgcaga caagaaggcc     600
gctgatatgc ttgctgaata cgagcgcaga aaaggtattc tggacacccg gttgtcagag     660
ctggaaaaaa atgcgggggc agcccttgcc gttcttgatg cacaacaggc ccgtctgctc     720
gggcagcaga cacggaatga cagggccatt tcagaggccc ggaataaact cagttcagtg     780
acggaatcgc ttaacacggc ccgtaatgca ttaaccagag ctgaacaaca gctgacgcaa     840
cagaaaaaca cgcctgacgg caaaacgata gtttcccctg aaaaattccc ggggcgttca     900
tcaacaaatc attctattgt tgtgagcggt gatccgagat ttgccggtac gataaaaatc     960
acaaccagcg cagtcatcga taaccgtgca aacctgaatt atcttctgag ccattccggt    1020
ctggactata aacgcaatat tctgaatgac cggaatccgg tggtgacaga ggatgtggaa    1080
ggtgacaaga aaatttataa tgctgaagtt gctgaatggg ataagttacg gcaaagattg    1140
```

```
cttgatgcca gaaataaaat cacctctgct gaatctgcgg taaattcggc gagaaataac    1200
ctcagtgcca gaacaaatga gcaaaagcat gcaaatgacg ctcttaatgc cctgttgaag    1260 gaaaagaga atatacgtaa ccagctttcc ggcatcaatc agaagatagc ggaagagaaa    1320 agaaacagg atgaactgaa ggcaacgaaa gacgcaatta atttcacaac agagttcctg    1380
aaatcagttt cagaaaaata tggtgcaaaa gctgagcagt tagccagaga gatggccggg    1440
caggctaaag ggaagaaaat acgtaatgtt gaagaggcat taaaaacgta tgaaaagtac    1500
cgggctgaca ttaacaaaaa aattaatgca aaagatcgtg cagcgattgc cgcagcccct    1560
gagtctgtga agctgtctga tatatcgtct aatctgaaca gattcagtcg gggactggga    1620
tatgcaggaa aatttacaag tcttgctgac tggatcactg agtttggtaa ggctgtccgg    1680
acagagaact ggcgtcctct ttttgttaaa acagaaacca tcatagcagg caatgccgca    1740
acggctcttg tggcactggt cttcagtatt cttaccggaa gcgctttagg cattatcggg    1800
tatggtttac tgatggctgt caccggtgcg ctgattgatg aatcgcttgt ggaaaaagcg    1860
aataagttct ggggttattc cacctgtgat tttataatga tt                       1902

<210> SEQ ID NO 19
<211> LENGTH: 633
<212> TYPE: PRT
<213> ORGANISM: Artificial Sequence
<220> FEATURE:
<223> OTHER INFORMATION: The peptide of PMC-SA4

<400> SEQUENCE: 19

Ser Asp Pro Val Arg Ile Thr Asn Pro Ala Ala Glu Ser Leu Gly Tyr
1               5                   10                  15

Asp Ser Asp Gly Arg Glu Ile Met Gly Val Asp Ile Tyr Leu Asn Pro
            20                  25                  30

Pro Arg Val Asp Val Phe Lys Gly Thr Pro Pro Ala Trp Ser Ser Phe
        35                  40                  45

Gly Asn Lys Thr Ile Trp Gly Gly Asn Glu Trp Val Asp Asp Ser Pro
    50                  55                  60

Thr Arg Ser Asp Ile Glu Lys Arg Asp Lys Glu Ile Thr Ala Tyr Lys
65                  70                  75                  80

Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
        115                 120                 125

Thr Arg Gln Glu Phe Arg Leu Leu Gln Ala Glu Leu Arg Glu Tyr Gly
    130                 135                 140

Phe Arg Thr Glu Ile Ala Gly Tyr Asp Ala Leu Arg Leu His Thr Glu
145                 150                 155                 160

Ser Arg Met Leu Phe Ala Asp Ala Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
        195                 200                 205

Arg Lys Gly Ile Leu Asp Thr Arg Leu Ser Glu Leu Glu Lys Asn Gly
    210                 215                 220

Gly Ala Ala Leu Ala Val Leu Asp Ala Gln Gln Ala Arg Leu Leu Gly
```

```
                225                 230                 235                 240
Gln Gln Thr Arg Asn Asp Arg Ala Ile Ser Glu Ala Arg Asn Lys Leu
                245                 250                 255
Ser Ser Val Thr Glu Ser Leu Asn Thr Ala Arg Asn Ala Leu Thr Arg
                260                 265                 270
Ala Glu Gln Gln Leu Thr Gln Gln Lys Asn Thr Pro Asp Gly Lys Thr
                275                 280                 285
Ile Val Ser Pro Glu Lys Phe Pro Gly Arg Ser Ser Thr Asn His Ser
                290                 295                 300
Ile Val Val Ser Gly Asp Pro Arg Phe Ala Gly Thr Ile Lys Ile Thr
305                 310                 315                 320
Thr Ser Ala Val Ile Asp Asn Arg Ala Asn Leu Asn Tyr Leu Leu Ser
                325                 330                 335
His Ser Gly Leu Asp Tyr Lys Arg Asn Ile Leu Asn Asp Arg Asn Pro
                340                 345                 350
Val Val Thr Glu Asp Val Glu Gly Asp Lys Lys Ile Tyr Asn Ala Glu
                355                 360                 365
Val Ala Glu Trp Asp Lys Leu Arg Gln Arg Leu Leu Asp Ala Arg Asn
                370                 375                 380
Lys Ile Thr Ser Ala Glu Ser Ala Val Asn Ser Ala Arg Asn Asn Leu
385                 390                 395                 400
Ser Ala Arg Thr Asn Glu Gln Lys His Ala Asn Asp Ala Leu Asn Ala
                405                 410                 415
Leu Leu Lys Glu Lys Glu Asn Ile Arg Asn Gln Leu Ser Gly Ile Asn
                420                 425                 430
Gln Lys Ile Ala Glu Glu Lys Arg Lys Gln Asp Glu Leu Lys Ala Thr
                435                 440                 445
Lys Asp Ala Ile Asn Phe Thr Thr Glu Phe Leu Lys Ser Val Ser Glu
                450                 455                 460
Lys Tyr Gly Ala Lys Ala Glu Gln Leu Ala Arg Glu Met Ala Gly Gln
465                 470                 475                 480
Ala Lys Gly Lys Lys Ile Arg Asn Val Glu Glu Ala Leu Lys Thr Tyr
                485                 490                 495
Glu Lys Tyr Arg Ala Asp Ile Asn Lys Lys Ile Asn Ala Lys Asp Arg
                500                 505                 510
Ala Ala Ile Ala Ala Ala Leu Glu Ser Val Lys Leu Ser Asp Ile Ser
                515                 520                 525
Ser Asn Leu Asn Arg Phe Ser Arg Gly Leu Gly Tyr Ala Gly Lys Phe
                530                 535                 540
Thr Ser Leu Ala Asp Trp Ile Thr Glu Phe Gly Lys Ala Val Arg Thr
545                 550                 555                 560
Glu Asn Trp Arg Pro Leu Phe Val Lys Thr Glu Thr Ile Ile Ala Gly
                565                 570                 575
Asn Ala Ala Thr Ala Leu Val Ala Leu Val Phe Ser Ile Leu Thr Gly
                580                 585                 590
Ser Ala Leu Gly Ile Ile Gly Tyr Gly Leu Leu Met Ala Val Thr Gly
                595                 600                 605
Ala Leu Ile Asp Glu Ser Leu Val Glu Lys Ala Asn Lys Phe Trp Gly
                610                 615                 620
Ile Tyr Ser Thr Cys Tyr Phe Ile Met
625                 630

<210> SEQ ID NO 20
<211> LENGTH: 1902
```

<212> TYPE: DNA
<213> ORGANISM: Artificial Sequence
<220> FEATURE:
<223> OTHER INFORMATION: Gene encoding the novel antibiotic PMC-SE

<400> SEQUENCE: 20

```
atgtctgacc ctgtacgtat tacaaatccc gcagcagaat cgctggggta tgattcagat      60
ggcaaagaaa ttatgggtgt tgatatttat ctcaaccctc cacgtgtcga tgtctttaaa     120
ggtaccccgc ctgcatggag ttccttcggg aacaaaacca tctggggcgg aaacgagtgg     180
gttgatgatt ccccaacccg aagtgatatc gaaaaaaggg acaaggaaat cacagcgtac     240
aaaaacacgc tcagcgcgca gcagaaagag aatgagaata agcgtactga agccggaaaa     300
cgcctctctg cggcgattgc tgcaaggaa aaagatgaaa acacactgaa aacactccgt      360
gccggaaacg cagatgccgc tgatattaca cgacaggagt tcagactcct gcaggcagag     420
ctgagagaat acggattccg tactgaaatc gccggatatg acgccctccg gctgcataca     480
gagagccgga tgctgtttgc tgatgctgat tctcttcgta tatctccccg ggaggccagg     540
tcgttaatcg aacaggctga aaacggcag aaggatgcgc agaacgcaga caagaaggcc      600
gctgatatgc ttgctgaata cgagcgcaga aaggtattc tggacacccg gttgtcagag      660
ctggaaaaaa atggcggggc agcccttgcc gttcttgatg cacaacaggc ccgtctgctc     720
gggcagcaga cacggaatga cagggccatt tcagaggccc ggaataaact cagttcagtg     780
acggaatcgc ttaacacggc ccgtaatgca ttaaccagag ctgaacaaca gctgacgcaa     840
cagaaaaaca cgcctgacgg caaaacgata gtttcccctg aaaaattccc ggggcgttca     900
tcaacaaatc attctattgt tgtgagcggt gatccgagat ttgccggtac gataaaaatc     960
acaaccagcg cagtcatcga taaccgtgca aacctgaatt atcttctgag ccattccggt    1020
ctggactata aacgcaatat tctgaatgac cggaatccgg tggtgacaga ggatgtggaa    1080
ggtgacaaga aaatttataa tgctgaagtt gctgaatggg ataagttacg gcaaagattg    1140
cttgatgcca gaaataaaat cacctctgct gaatctgcgg taaattcggc gagaaataac    1200
ctcagtgcca aacaaatga gcaaaagcat gcaaatgacg ctcttaatgc cctgttgaag    1260
gaaaagaga atatacgtaa ccagctttcc ggcatcaatc agaagatagc ggaagagaaa    1320
agaaaacagg atgaactgaa ggcaacgaaa gacgcaatta atttcacaac agagttcctg    1380
aaatcagttt cagaaaaata tggtgcaaaa gctgagcagt tagccagaga gatggccggg    1440
caggctaaag ggaagaaaat acgtaatgtt gaagaggcat taaaaacgta tgaaaagtac    1500
cgggctgaca ttaacaaaaa aattaatgca aaagatcgtg cagcgattgc cgcagcccttt   1560
gagtctgtga agctgtctga tatatcgtct aatctgaaca gattcagtcg gggactggga    1620
tatgcaggaa aatttacaag tcttgctgac tggatcactg agtttggtaa ggctgtccgg    1680
acagagaact ggcgtcctct ttttgttaaa acagaaacca tcatagcagg caatgccgca    1740
acggctcttg tggcactggt cttcagtatt cttaccggaa gcgctttagg cattatcggg    1800
tatggtttac tgatggctgt caccggtgcg ctgattgatg aatcgcttgt ggaaaaagcg    1860
aataagttct ggggtgattc cgtttgtgca tcctatttta tt                       1902
```

<210> SEQ ID NO 21
<211> LENGTH: 633
<212> TYPE: PRT
<213> ORGANISM: Artificial Sequence
<220> FEATURE:
<223> OTHER INFORMATION: The peptide of PMC-SE

<400> SEQUENCE: 21

-continued

```
Ser Asp Pro Val Arg Ile Thr Asn Pro Ala Ala Glu Ser Leu Gly Tyr
1               5                   10                  15

Asp Ser Asp Gly Arg Glu Ile Met Gly Val Asp Ile Tyr Leu Asn Pro
            20                  25                  30

Pro Arg Val Asp Val Phe Lys Gly Thr Pro Pro Ala Trp Ser Ser Phe
        35                  40                  45

Gly Asn Lys Thr Ile Trp Gly Gly Asn Glu Trp Val Asp Asp Ser Pro
    50                  55                  60

Thr Arg Ser Asp Ile Glu Lys Arg Asp Lys Glu Ile Thr Ala Tyr Lys
65                  70                  75                  80

Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
        115                 120                 125

Thr Arg Gln Glu Phe Arg Leu Leu Gln Ala Glu Leu Arg Glu Tyr Gly
    130                 135                 140

Phe Arg Thr Glu Ile Ala Gly Tyr Asp Ala Leu Arg Leu His Thr Glu
145                 150                 155                 160

Ser Arg Met Leu Phe Ala Asp Ala Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
        195                 200                 205

Arg Lys Gly Ile Leu Asp Thr Arg Leu Ser Glu Leu Glu Lys Asn Gly
    210                 215                 220

Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
                245                 250                 255

Ser Ser Val Thr Glu Ser Leu Asn Thr Ala Arg Asn Ala Leu Thr Arg
            260                 265                 270

Ala Glu Gln Gln Leu Thr Gln Gln Lys Asn Thr Pro Asp Gly Lys Thr
        275                 280                 285

Ile Val Ser Pro Glu Lys Phe Pro Gly Arg Ser Ser Thr Asn His Ser
    290                 295                 300

Ile Val Val Ser Gly Asp Pro Arg Phe Ala Gly Thr Ile Lys Ile Thr
305                 310                 315                 320

Thr Ser Ala Val Ile Asp Asn Arg Ala Asn Leu Asn Tyr Leu Leu Ser
                325                 330                 335

His Ser Gly Leu Asp Tyr Lys Arg Asn Ile Leu Asn Asp Arg Asn Pro
            340                 345                 350

Val Val Thr Glu Asp Val Glu Gly Asp Lys Lys Ile Tyr Asn Ala Glu
        355                 360                 365

Val Ala Glu Trp Asp Lys Leu Arg Gln Arg Leu Leu Asp Ala Arg Asn
    370                 375                 380

Lys Ile Thr Ser Ala Glu Ser Ala Val Asn Ser Ala Arg Asn Asn Leu
385                 390                 395                 400

Ser Ala Arg Thr Asn Glu Gln Lys His Ala Asn Asp Ala Leu Asn Ala
                405                 410                 415

Leu Leu Lys Glu Lys Glu Asn Ile Arg Asn Gln Leu Ser Gly Ile Asn
```

```
                   420              425               430
Gln Lys Ile Ala Glu Glu Lys Arg Lys Gln Asp Glu Leu Lys Ala Thr
            435                 440                 445

Lys Asp Ala Ile Asn Phe Thr Thr Glu Phe Leu Lys Ser Val Ser Glu
    450                 455                 460

Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
                485                 490                 495

Glu Lys Tyr Arg Ala Asp Ile Asn Lys Lys Ile Asn Ala Lys Asp Arg
            500                 505                 510

Ala Ala Ile Ala Ala Ala Leu Glu Ser Val Lys Leu Ser Asp Ile Ser
        515                 520                 525

Ser Asn Leu Asn Arg Phe Ser Arg Gly Leu Gly Tyr Ala Gly Lys Phe
    530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
                565                 570                 575

Asn Ala Ala Thr Ala Leu Val Ala Leu Val Phe Ser Ile Leu Thr Gly
            580                 585                 590

Ser Ala Leu Gly Ile Ile Gly Tyr Gly Leu Leu Met Ala Val Thr Gly
        595                 600                 605

Ala Leu Ile Asp Glu Ser Leu Val Glu Lys Ala Asn Lys Phe Trp Gly
    610                 615                 620

Ile Asp Ser Val Cys Ala Ser Tyr Phe
625                 630

<210> SEQ ID NO 22
<211> LENGTH: 1902
<212> TYPE: DNA
<213> ORGANISM: Artificial Sequence
<220> FEATURE:
<223> OTHER INFORMATION: Gene encoding the novel antibiotic PMC-SA

<400> SEQUENCE: 22
atgtattcca cctgtgattt tataatgtct gaccctgtac gtattacaaa tcccgcagca      60
gaatcgctgg ggtatgattc agatggcaaa gaaattatgg gtgttgatat ttatctcaac     120
cctccacgtg tcgatgtctt taaaggtacc ccgcctgcat ggagttcctt cgggaacaaa     180
accatctggg gcggaaacga gtgggttgat gattccccaa cccgaagtga tatcgaaaaa     240
agggacaagg aaatcacagc gtacaaaaac acgctcagcg cgcagcagaa agagaatgag     300
aataagcgta ctgaagccgg aaaacgcctc tctgcggcga ttgctgcaag ggaaaaagat     360
gaaaacacac tgaaaacact ccgtgccgga acgcagatgc cgctgatat  acacgacag     420 gagttcagac tcctgcaggc agagctgaga gaatacggat tccgtactga aatcgccgga     480
tatgacgccc tccggctgca tacagagagc cggatgctgt tgctgatgc  tgattctctt     540 cgtatatctc cccgggaggc caggtcgtta atcgaacagg ctgaaaaacg gcagaaggat     600
gcgcagaacg cagacaagaa ggccgctgat atgcttgctg aatacgagcg cagaaaaggt     660
attctggaca cccggttgtc agagctggaa aaaaatggcg gggcagccct tgccgttctt     720
gatgcacaac aggcccgtct gctcgggcag cagacacgga atgacagggc catttcagag     780
gcccggaata aactcagttc agtgacggaa tcgcttaaca cggcccgtaa tgcattaacc     840
agagctgaac aacagctgac gcaacagaaa aacacgcctg acggcaaaac gatagtttcc     900
```

```
cctgaaaaat tcccggggcg ttcatcaaca aatcattcta ttgttgtgag cggtgatccg      960
agatttgccg gtacgataaa aatcacaacc agcgcagtca tcgataaccg tgcaaacctg     1020
aattatcttc tgagccattc cggtctggac tataaacgca atattctgaa tgaccggaat     1080
ccggtggtga cagaggatgt ggaaggtgac aagaaaattt ataatgctga agttgctgaa     1140
tgggataagt tacggcaaag attgcttgat gccagaaata aaatcacctc tgctgaatct     1200
gcggtaaatt cggcgagaaa taacctcagt gccagaacaa atgagcaaaa gcatgcaaat     1260
gacgctctta atgcccctgtt gaaggaaaaa gagaatatac gtaaccagct ttccggcatc     1320
aatcagaaga tagcggaaga gaaagaaaa caggatgaac tgaaggcaac gaaagacgca      1380
attaatttca caacagagtt cctgaaatca gtttcagaaa aatatggtgc aaaagctgag     1440
cagttagcca gagagatggc cgggcaggct aaagggaaga aaatacgtaa tgttgaagag     1500
gcattaaaaa cgtatgaaaa gtaccgggct gacattaaca aaaaaattaa tgcaaaagat     1560
cgtgcagcga ttgccgcagc ccttgagtct gtgaagctgt ctgatatatc gtctaatctg     1620
aacagattca gtcggggact gggatatgca ggaaaattta caagtcttgc tgactggatc     1680
actgagtttg gtaaggctgt ccggacagag aactggcgtc ctcttttgt taaaacagaa      1740 accatcatag caggcaatgc cgcaacggct cttgtggcac tggtcttcag tattcttacc     1800
ggaagcgctt taggcattat cgggtatggt ttactgatgg ctgtcaccgg tgcgctgatt     1860
gatgaatcgc ttgtggaaaa agcgaataag ttctggggta tt                       1902
```

<210> SEQ ID NO 23
<211> LENGTH: 633
<212> TYPE: PRT
<213> ORGANISM: Artificial Sequence
<220> FEATURE:
<223> OTHER INFORMATION: The peptide of PMC-SA

<400> SEQUENCE: 23

```
Tyr Ser Thr Cys Asp Phe Ile Met Ser Asp Pro Val Arg Ile Thr Asn
1               5                   10                  15

Pro Ala Ala Glu Ser Leu Gly Tyr Asp Ser Asp Gly Arg Glu Ile Met
            20                  25                  30

Gly Val Asp Ile Tyr Leu Asn Pro Pro Arg Val Asp Val Phe Lys Gly
        35                  40                  45

Thr Pro Pro Ala Trp Ser Ser Phe Gly Asn Lys Thr Ile Trp Gly Gly
    50                  55                  60

Asn Glu Trp Val Asp Asp Ser Pro Thr Arg Ser Asp Ile Glu Lys Arg
65                  70                  75                  80

Asp Lys Glu Ile Thr Ala Tyr Lys Asn Thr Leu Ser Ala Gln Gln Lys
                85                  90                  95

Glu Asn Glu Asn Lys Arg Thr Glu Ala Gly Lys Arg Leu Ser Ala Ala
            100                 105                 110

Ile Ala Ala Arg Glu Lys Asp Glu Asn Thr Leu Lys Thr Leu Arg Ala
        115                 120                 125

Gly Asn Ala Asp Ala Ala Asp Ile Thr Arg Gln Glu Phe Arg Leu Leu
    130                 135                 140

Gln Ala Glu Leu Arg Glu Tyr Gly Phe Arg Thr Glu Ile Ala Gly Tyr
145                 150                 155                 160

Asp Ala Leu Arg Leu His Thr Glu Ser Arg Met Leu Phe Ala Asp Ala
                165                 170                 175

Asp Ser Leu Arg Ile Ser Pro Arg Glu Ala Arg Ser Leu Ile Glu Gln
            180                 185                 190
```

```
Ala Glu Lys Arg Gln Lys Asp Ala Gln Asn Ala Asp Lys Ala Ala
        195                 200                 205
Asp Met Leu Ala Glu Tyr Glu Arg Lys Gly Ile Leu Asp Thr Arg
        210                 215                 220
Leu Ser Glu Leu Glu Lys Asn Gly Gly Ala Leu Ala Val Leu Asp
225                 230                 235                 240
Ala Gln Gln Ala Arg Leu Leu Gly Gln Gln Thr Arg Asn Asp Arg Ala
                245                 250                 255
Ile Ser Glu Ala Arg Asn Lys Leu Ser Ser Val Thr Glu Ser Leu Asn
                260                 265                 270
Thr Ala Arg Asn Ala Leu Thr Arg Ala Glu Gln Gln Leu Thr Gln Gln
        275                 280                 285
Lys Asn Thr Pro Asp Gly Lys Thr Ile Val Ser Pro Glu Lys Phe Pro
        290                 295                 300
Gly Arg Ser Ser Thr Asn His Ser Ile Val Ser Gly Asp Pro Arg
305                 310                 315                 320
Phe Ala Gly Thr Ile Lys Ile Thr Thr Ser Ala Val Ile Asp Asn Arg
                325                 330                 335
Ala Asn Leu Asn Tyr Leu Leu Ser His Ser Gly Leu Asp Tyr Lys Arg
                340                 345                 350
Asn Ile Leu Asn Asp Arg Asn Pro Val Val Thr Glu Asp Val Glu Gly
        355                 360                 365
Asp Lys Lys Ile Tyr Asn Ala Glu Val Ala Glu Trp Asp Lys Leu Arg
        370                 375                 380
Gln Arg Leu Leu Asp Ala Arg Asn Lys Ile Thr Ser Ala Glu Ser Ala
385                 390                 395                 400
Val Asn Ser Ala Arg Asn Asn Leu Ser Ala Arg Thr Asn Glu Gln Lys
                405                 410                 415
His Ala Asn Asp Ala Leu Asn Ala Leu Leu Lys Glu Lys Glu Asn Ile
                420                 425                 430
Arg Asn Gln Leu Ser Gly Ile Asn Gln Lys Ile Ala Glu Glu Lys Arg
        435                 440                 445
Lys Gln Asp Glu Leu Lys Ala Thr Lys Asp Ala Ile Asn Phe Thr Thr
        450                 455                 460
Glu Phe Leu Lys Ser Val Ser Glu Lys Tyr Gly Ala Lys Ala Glu Gln
465                 470                 475                 480
Leu Ala Arg Glu Met Ala Gly Gln Ala Lys Gly Lys Lys Ile Arg Asn
                485                 490                 495
Val Glu Glu Ala Leu Lys Thr Tyr Glu Lys Tyr Arg Ala Asp Ile Asn
                500                 505                 510
Lys Lys Ile Asn Ala Lys Asp Arg Ala Ala Ile Ala Ala Leu Glu
        515                 520                 525
Ser Val Lys Leu Ser Asp Ile Ser Ser Asn Leu Asn Arg Phe Ser Arg
        530                 535                 540
Gly Leu Gly Tyr Ala Gly Lys Phe Thr Ser Leu Ala Asp Trp Ile Thr
545                 550                 555                 560
Glu Phe Gly Lys Ala Val Arg Thr Glu Asn Trp Arg Pro Leu Phe Val
                565                 570                 575
Lys Thr Glu Thr Ile Ile Ala Gly Asn Ala Ala Thr Ala Leu Val Ala
        580                 585                 590
Leu Val Phe Ser Ile Leu Thr Gly Ser Ala Leu Gly Ile Ile Gly Tyr
        595                 600                 605
Gly Leu Leu Met Ala Val Thr Gly Ala Leu Ile Asp Glu Ser Leu Val
```

Glu Lys Ala Asn Lys Phe Trp Gly Ile
625              630

<210> SEQ ID NO 24
<211> LENGTH: 66
<212> TYPE: DNA
<213> ORGANISM: Staphylococcus aureaus
<220> FEATURE:
<223> OTHER INFORMATION: 5' primer of gene of AgrDI

<400> SEQUENCE: 24
gcgaataagt tctggggtat ttattccacc tgtgatttta taatgtaaat aaaatataag    60
acaggc                                                              66

<210> SEQ ID NO 25
<211> LENGTH: 66
<212> TYPE: DNA
<213> ORGANISM: Staphylococcus aureaus
<220> FEATURE:
<223> OTHER INFORMATION: 3' primer of gene of AgrDI

<400> SEQUENCE: 25
gcctgtctta tattttattt acattataaa atcacaggtg aataaatac cccagaactt    60 attcgc                                                              66

<210> SEQ ID NO 26
<211> LENGTH: 69
<212> TYPE: DNA
<213> ORGANISM: Staphylococcus aureaus
<220> FEATURE:
<223> OTHER INFORMATION: 5' primer of gene of AgrDII

<400> SEQUENCE: 26
gcgaataagt tctggggtat tggagttaac gcatgttctt ccctgtttta aataaaatat    60
aagacaggc                                                           69

<210> SEQ ID NO 27
<211> LENGTH: 69
<212> TYPE: DNA
<213> ORGANISM: Staphylococcus aureaus
<220> FEATURE:
<223> OTHER INFORMATION: 3' primer of gene of AgrDII

<400> SEQUENCE: 27
gcctgtctta tattttattt aaaacaggga agaacatgcg ttaactccaa taccccagaa    60
cttattcgc                                                           69

<210> SEQ ID NO 28
<211> LENGTH: 66
<212> TYPE: DNA
<213> ORGANISM: Staphylococcus aureaus
<220> FEATURE:
<223> OTHER INFORMATION: 5' primer of gene of AgrD III

<400> SEQUENCE: 28
gcgaataagt tctggggtat ttatataaac tgtgattttc ttctgtaaat aaaatataag    60
acaggc                                                              66

<210> SEQ ID NO 29
<211> LENGTH: 66
<212> TYPE: DNA
<213> ORGANISM: Staphylococcus aureaus

```
-continued

<220> FEATURE:
<223> OTHER INFORMATION: 3' primer of gene of AgrD III

<400> SEQUENCE: 29
gcctgtctta tattttattt acagaagaaa atcacagttt atataaatac cccagaactt    60
attcgc                                                               66

<210> SEQ ID NO 30
<211> LENGTH: 66
<212> TYPE: DNA
<213> ORGANISM: Staphylococcus aureaus
<220> FEATURE:
<223> OTHER INFORMATION: 5' primer of gene of AgrD IV

<400> SEQUENCE: 30
gcgaataagt tctggggtat ttattccacc tgttacttta taatgtaaat aaaatataag    60
acaggc                                                               66

<210> SEQ ID NO 31
<211> LENGTH: 66
<212> TYPE: DNA
<213> ORGANISM: Staphylococcus aureaus
<220> FEATURE:
<223> OTHER INFORMATION: 3' primer of gene of AgrD IV

<400> SEQUENCE: 31
gcctgtctta tattttattt acattataaa gtaacaggtg gaataaatac cccagaactt    60
attcgc                                                               66

<210> SEQ ID NO 32
<211> LENGTH: 66
<212> TYPE: DNA
<213> ORGANISM: Artificial Sequence
<220> FEATURE:
<223> OTHER INFORMATION: 5' primer of gene of AgrDI for preparing PMC-PA

<400> SEQUENCE: 32
ggatgaagga gataccgaat gtattccacc tgtgatttta taatgtctga ccctgtacgt    60
attaca                                                               66

<210> SEQ ID NO 33
<211> LENGTH: 66
<212> TYPE: DNA
<213> ORGANISM: ARtificial Sequence
<220> FEATURE:
<223> OTHER INFORMATION: 3' primer of gene of AgrDI for preparing PMC-PA

<400> SEQUENCE: 33
gtgaatacgt acagggtcag acattataaa atcacaggtg gaatacattc ggtatctcct    60
tcatcc                                                               66

<210> SEQ ID NO 34
<211> LENGTH: 66
<212> TYPE: DNA
<213> ORGANISM: Artificial Sequence
<220> FEATURE:
<223> OTHER INFORMATION: 5' primer of gene of Staphylococcus epidermidis
      pheromone

<400> SEQUENCE: 34
gcgaataagt tctggggtat tgattccgtt tgtgcatcct attttaaat aaaatataag     60 acaggc                                                               66
```

<210> SEQ ID NO 35
<211> LENGTH: 66
<212> TYPE: DNA
<213> ORGANISM: Artificial Sequence
<220> FEATURE:
<223> OTHER INFORMATION: 3'primer of gene of Staphylococcus epidermidis pheromone

<400> SEQUENCE: 35
gcctgtctta tattttattt aaaaatagga tgcacaaacg gaatcaatac cccagaactt    60
attcgc    66

<210> SEQ ID NO 36
<211> LENGTH: 625
<212> TYPE: PRT
<213> ORGANISM: Artificial Sequence
<220> FEATURE:
<223> OTHER INFORMATION: allosteric peptide of colicin Ia

<400> SEQUENCE: 36

```
Ser Asp Pro Val Arg Ile Thr Asn Pro Ala Ala Glu Ser Leu Gly Tyr
1               5                   10                  15

Asp Ser Asp Gly Arg Glu Ile Met Gly Val Asp Ile Tyr Leu Asn Pro
            20                  25                  30

Pro Arg Val Asp Val Phe Lys Gly Thr Pro Pro Ala Trp Ser Ser Phe
        35                  40                  45

Gly Asn Lys Thr Ile Trp Gly Gly Asn Glu Trp Val Asp Asp Ser Pro
    50                  55                  60

Thr Arg Ser Asp Ile Glu Lys Arg Asp Lys Glu Ile Thr Ala Tyr Lys
65                  70                  75                  80

Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
        115                 120                 125

Thr Arg Gln Glu Phe Arg Leu Leu Gln Ala Glu Leu Arg Glu Tyr Gly
    130                 135                 140

Phe Arg Thr Glu Ile Ala Gly Tyr Asp Ala Leu Arg Leu His Thr Glu
145                 150                 155                 160

Ser Arg Met Leu Phe Ala Asp Ala Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
        195                 200                 205

Arg Lys Gly Ile Leu Asp Thr Arg Leu Ser Glu Leu Glu Lys Asn Gly
    210                 215                 220

Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
                245                 250                 255

Ser Ser Val Thr Glu Ser Leu Asn Thr Ala Arg Asn Ala Leu Thr Arg
            260                 265                 270

Ala Glu Gln Gln Leu Thr Gln Gln Lys Asn Thr Pro Asp Gly Lys Thr
        275                 280                 285

Ile Val Ser Pro Glu Lys Phe Pro Gly Arg Ser Ser Thr Asn His Ser
```

```
                290            295            300
Ile Val Val Ser Gly Asp Pro Arg Phe Ala Gly Thr Ile Lys Ile Thr
305            310            315            320

Thr Ser Ala Val Ile Asp Asn Arg Ala Asn Leu Asn Tyr Leu Leu Ser
                325            330            335

His Ser Gly Leu Asp Tyr Lys Arg Asn Ile Leu Asn Asp Arg Asn Pro
            340            345            350

Val Val Thr Glu Asp Val Glu Gly Asp Lys Lys Ile Tyr Asn Ala Glu
        355            360            365

Val Ala Glu Trp Asp Lys Leu Arg Gln Arg Leu Leu Asp Ala Arg Asn
370            375            380

Lys Ile Thr Ser Ala Glu Ser Ala Val Asn Ser Ala Arg Asn Asn Leu
385            390            395            400

Ser Ala Arg Thr Asn Glu Gln Lys His Ala Asn Asp Ala Leu Asn Ala
                405            410            415

Leu Leu Lys Glu Lys Glu Asn Ile Arg Asn Gln Leu Ser Gly Ile Asn
            420            425            430

Gln Lys Ile Ala Glu Glu Lys Arg Lys Gln Asp Glu Leu Lys Ala Thr
        435            440            445

Lys Asp Ala Ile Asn Phe Thr Thr Glu Phe Leu Lys Ser Val Ser Glu
450            455            460

Lys Tyr Gly Ala Lys Ala Glu Gln Leu Ala Arg Glu Met Ala Gly Gln
465            470            475            480

Ala Lys Gly Lys Lys Ile Arg Asn Val Glu Glu Ala Leu Lys Thr Tyr
                485            490            495

Glu Lys Tyr Arg Ala Asp Ile Asn Lys Lys Ile Asn Ala Lys Asp Arg
            500            505            510

Ala Ala Ile Ala Ala Ala Leu Glu Ser Val Lys Leu Ser Asp Ile Ser
        515            520            525

Ser Asn Leu Asn Arg Phe Ser Arg Gly Leu Gly Tyr Ala Gly Lys Phe
530            535            540

Thr Ser Leu Ala Asp Trp Ile Thr Glu Phe Gly Lys Ala Val Arg Thr
545            550            555            560

Glu Asn Trp Arg Pro Leu Phe Val Lys Thr Glu Thr Ile Ile Ala Gly
                565            570            575

Asn Ala Ala Thr Ala Leu Val Ala Leu Val Phe Ser Ile Leu Thr Gly
            580            585            590

Ser Ala Leu Gly Ile Ile Gly Tyr Gly Leu Leu Met Ala Val Thr Gly
        595            600            605

Ala Leu Ile Asp Glu Ser Leu Val Glu Lys Ala Asn Lys Phe Trp Gly
610            615            620

Ile
625

<210> SEQ ID NO 37
<211> LENGTH: 8
<212> TYPE: PRT
<213> ORGANISM: Staphylococcus epidermidis
<220> FEATURE:
<223> OTHER INFORMATION: Peptide of Staphylococcus epidermidis pheromone

<400> SEQUENCE: 37

Asp Ser Val Cys Ala Ser Tyr Phe
1               5
```